(12) United States Patent
Champagne et al.

(10) Patent No.: US 9,487,790 B2
(45) Date of Patent: Nov. 8, 2016

(54) NUCLEAR BASED EXPRESSION OF GENES FOR PRODUCTION OF BIOFUELS AND PROCESS CO-PRODUCTS IN ALGAE

(75) Inventors: Michele M. Champagne, Honolulu, HI (US); Adelheid R. Kuehnle, Honolulu, HI (US)

(73) Assignee: Kuehnle AgroSystems, Inc., Honolulu, HI (US)

( * ) Notice: Subject to any disclaimer, the term of this patent is extended or adjusted under 35 U.S.C. 154(b) by 468 days.

(21) Appl. No.: 12/415,904

(22) Filed: Mar. 31, 2009

(65) Prior Publication Data

US 2009/0317878 A1 Dec. 24, 2009

Related U.S. Application Data

(60) Provisional application No. 61/041,062, filed on Mar. 31, 2008.

(51) Int. Cl.
| | | |
|---|---|---|
| *C12N 15/86* | (2006.01) | |
| *A01G 33/00* | (2006.01) | |
| *C02F 3/34* | (2006.01) | |
| *C12N 15/70* | (2006.01) | |
| *C12N 15/52* | (2006.01) | |
| *C12N 15/79* | (2006.01) | |
| *C12N 1/12* | (2006.01) | |

(52) U.S. Cl.
CPC .............. *C12N 15/79* (2013.01); *C12N 1/12* (2013.01)

(58) Field of Classification Search
None
See application file for complete search history.

(56) References Cited

U.S. PATENT DOCUMENTS

| 6,252,140 B1 * | 6/2001 | Mitra et al. ............... 800/298 |
| 7,129,391 B1 * | 10/2006 | Daniell ..................... 800/278 |
| 2006/0115545 A1 | 6/2006 | Frohberg et al. |
| 2006/0143732 A1 * | 6/2006 | Perez et al. ............... 800/278 |

OTHER PUBLICATIONS

Graves et al. "Characterization of the major capsid protein and cloning of its gene from algal virus PBCV-1." Virology. 188(1):198-207 (1992).
Kim et al. "Natural History of Transposition in the Green Alga *Chlamydomonas reinhardtii*: Use of the AMT4 Locus as an Experimental System." Genetics. 173:2005-2019 (Aug. 2006).
Kindle et al. "Stable nuclear transformation of Chlamydomonas using the Chlamydomonas gene for nitrate reductase." The Journal of Cell Biology. 109(6)(Pt.1):2589-2601 (Dec. 1989).
Koblenz et al. "The NIT1 promoter allows inducible and reversible silencing of centrin in Chlamydomonas reinhardtii." Eukaryotic Cell. p. 1959-1962 (Nov. 2005).
Ohresser et al. "Expression of the arylsulphatase reporter gene under the control of the nit1 promoter in Chlamydomonas reinhardtii." Current Genetics. 31(3):264-271 (1997).
Ruecker et al. "Gaussia-luciferase as a sensitive reporter gene for monitoring promoter activity in the nucleus of the green alga *Chlamydomonas reinhardtii*." Mol Genet Genomics. 280:153-162 (2008).
Walker, Tara L. "The Development of Microalgae as a Bioreactor System for the Production of Recombinant Proteins." Thesis, online: URL:http://eprints.qut.edu.au/15905/1/Tara_Walker_Thesis.pdf>. Jan. 1, 2003.
Supplementary European Search Report for European Application No. EP 09727734 dated Apr. 29, 2011, (4 pages).
Urawa et al: "Enhanced homologues recombination caused by the non-transcribed spacer of the rRNA in Arabidopsis", Molecular genetics and genomics, vol. 266, No. 4, Dec. 1, 2001, pp. 546-555.
Official Communication pursuant to Article 94(3) EPC dated Nov. 2, 2012 for European Application No. 09727734.7, 2 pages.
Paule et al., "Survey and Summary Transcription by RNA polymerases I and III", Nucleic Acids Research, 2000, vol. 28, No. 6, pp. 1283-1298.
Borisjuk et al., "Structural analysis of rDNA in the genus *Nicotiana*", Plant Molecular Biology, vol. 35, pp. 655-660, 1997.
Castiglione et al., "Ribosomal RNA genes of Phaseolus coccineus—V. Relationship between rDNA phenotype and somatic differentiation", Protoplasma, 1998, vol. 203, pp. 75-83.
GenBank: AJ279508.1, "Chironomus cigulatus partial 28S rRNA gene, partial 18S Rrna gene and intergenic spacer (IGS), clone cinIGS 33", Oct. 23, 2008, Nucleotide—NCBI, http://www.ncbi.nlm.nih.gov/nuccore/AJ279508.1, 2 pages.
GenBank: AJ604561.1, "Marteilia refringens partial 28S rRNA gene, IGS, and partial 18S rRNA gene", Jan. 7, 2006, Nucleotide—NCBI, http://www.ncbi.nlm.nih.gov/nuccore/AJ604561.1, 2 pages.
GenBank: AJ854656.1, "Fusarium sporotrichioides partial 28S rRNA gene, IGS and partial 18S rRNA gene. Isolate CECT 20166", Jul. 7, 2005, Nucleotide—NCBI, http://www.ncbi.nlm.nih.gov/nuccore/AJ854656.1, 2 pages.
Maluszynska et al., "rRNA Genes—Their Distribution and Activity in Plants", Plant Cytogenetics. Katowice, 1998, pp. 75-96.
Powell et al., "Association Between rDNA Alleles and Quantitative Traits in Doubled Haploid Populations of Barley", Genetics, vol. 130, pp. 187-194, Jan. 1992.

* cited by examiner

*Primary Examiner* — Catherine S Hibbert
*Assistant Examiner* — Channing S Mahatan
(74) *Attorney, Agent, or Firm* — Knobbe, Martens, Olson & Bear, LLP

(57) ABSTRACT

Various embodiments provide, for example, vectors, expression cassettes, and cells useful for transgenic expression of nucleic acid sequences. In various embodiments, vectors can contain nuclear-based sequences of unicellular photosynthetic bioprocess organisms for the production of food- and feed-stuffs, oils, biofuels, starches, raw materials, pharmaceuticals or fine chemicals.

27 Claims, 1 Drawing Sheet

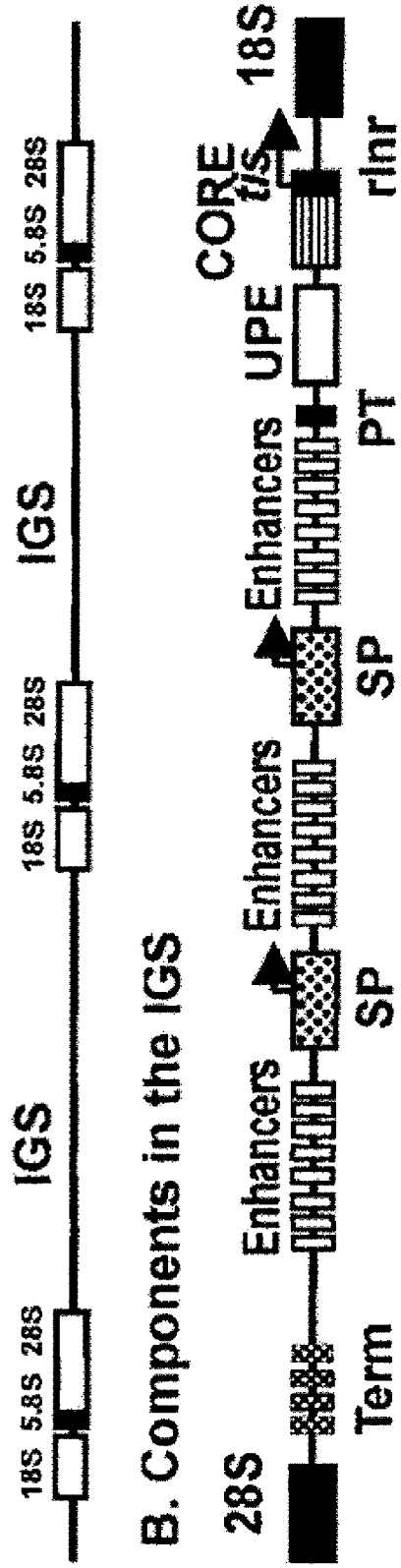

NUCLEAR BASED EXPRESSION OF GENES FOR PRODUCTION OF BIOFUELS AND PROCESS CO-PRODUCTS IN ALGAE

RELATED APPLICATIONS

The present application claims priority to U.S. Provisional Application Ser. No. 61/041,062, filed on Mar. 31, 2008, by Kuehnle et al., and entitled "NUCLEAR BASED EXPRESSION OF GENES FOR PRODUCTION OF BIOFUELS AND PROCESS CO-PRODUCTS IN ALGAE," the entire disclosure of which is herein incorporated by reference in its entirety.

BACKGROUND

1. Field

The present application pertains generally to expression of genes in algae. In particular, the application relates to methods and compositions for introduction of genes and regulatory sequences into the nucleus of bioprocess algae.

2. Description of the Related Art

Culturing microalgae under nitrogen starvation promotes a shift in algae metabolism, decreasing the rates of protein synthesis and cell division. A concomitant increase in the total cellular content of lipid arises as the cell division rate decreases more rapidly than the rate of lipid synthesis (Livne and Sukenik, 1992). Subsequently, fatty acid profiles change in a species-specific manner, but the general trend observed is a reduction in polyenoic fatty acids and polar lipids, and an increase in nonpolar storage lipids (Zhila et al., 2005; Guschina and Harwood, 2006).

Pond systems for algae oil production may be able to increase total output of lipids and other useful biomass by the use of a biphasic system (Huntley and Redaljie, 2007) that shortens the duration of cultivation in open ponds. This reduces the undesired side effects of competition from contaminating species. Culture expansion can proceed under nonlimiting conditions, followed by a brief nitrogen starvation and enhanced synthesis of lipids. Made-to-order biosynthesis of lipids and other high value coproducts can be accomplished by induction or repression of fatty acid or other biosynthetic genes under the control of nitrogen-responsive promoters. Key lipid biosynthetic enzymes to regulate by this strategy include, but are not limited to, fatty acid synthases (Bonaventure et al., 2003; Wu et al., 1994), desaturases (Pidkowich et al., 2007) or the rate-limiting step for total output, accD (reviewed in Rawsthorne, 2002).

Until now, nitrogen-inducible or nitrate-responsive promoters have not been utilized in algae for this purpose. Ammonium ($NH_4^+ + NH_3$) and nitrate ($NO_3^-$) are useful nitrogen sources for many microorganisms. High affinity ammonium transporters of the AMT/MEP family have been described at the molecular level in diverse organisms such as plants, yeast, bacteria, fungi and animals. The synthesis of structural and enzymatic genes required for nitrogen assimilation, such as $NH_3$ gas channels (Gonzalez-Ballester et al., 2004; Kim et al., 2005) and nitrate reductase (Fernandez et al., 1989; Franco et al., 1984) is directly influenced in algae by environmental $NH_3$ and $NO_3^-$ conditions and is regulated primarily by controlling transcription. In *Chlamydomonas*, the ammonium transporter genes AMT1, AMT2 and AMT 4 are tightly repressed in the presence of ammonium or nitrate, and rapidly induced to a high level of transcription, three or four orders of magnitude in its absence (Kim et al., 2005). Nitrate reductase, NIT1, is similarly repressed by ammonium but it is further de-repressed in the presence of nitrate or in nitrogen-free medium (Fernandez et al., 1989).

Similarly, large-scale algae culture farms are ideal for sequestration of excess $CO_2$ from point sources such as coal burning power plants. It is known that $CO_2$ supplementation of cultures promotes high rates of alga photosynthesis and growth, and may also enhance lipid synthesis as much as 30% (Murandyan et al., 2004). It would be useful to use $CO_2$ as an environmental signal for deliberate regulation of gene expression. However, until now, no $CO_2$-inducible promoters have been identified and utilized in algae for this purpose. Regulatory sequences from a natural $CO_2$ transporter system, such as Rh1, could provide a novel transgene expression system in algae that are responsive to varying algae culture conditions.

Other inducible promoter sequences useful for nuclear expression of genes for biofuels and process co-products include those responsive to light. For example, chlorophyll-binding proteins have been isolated, sequenced, and shown useful in diatoms for transgene expression.

Constitutive promoters are of interest in addition to inducible promoters for nuclear-based expression of genes. Constitutive viral promoter sequences have a long history of utility in biotechnology, effectively driving expression of transgenes in many in vivo culture platforms. In higher plants, pararetroviruses, such as Caulimovirus (CaMV) have proven especially useful. Although the host range of CaMV is restricted, its 35S rDNA promoter (Fang et al., 1989; Benfey et al., 1990) functions in many species of land plants and is used in most genetically modified crops (hypertext transfer protocol usbiotechreg.nbii.gov/). It has been used in the chlorophyte algae *Chlamydomonas* (Tang et al., 1995) and *Dunaliella* (Geng et al., 2003). This viral sequence was reported to work in the dinoflagellates *Amphidinium* and *Symbodinium* (Lohuis and Miller, 1998). However, it was not active when tested in the diatoms *Cyclotella* or *Navicula* (Dunahay et al., 1995). There is a clear need to discover promoter sequences from aquatic viruses, such as from the double-stranded DNA viruses in the *Phycodnaviridae*, as suitable substitutes for reliable and effective transgene expression in algae hosts. The *Chlorella* PBCV-1 virus produces more than 100 different proteins. The most abundant of these is the 54-kDa major coat protein, comprising more than 40 percent of the total mass of the virus. As such, it represents the most highly expressed protein gene and is an excellent candidate for driving constitutive expression of transgenes in Chlorophyte and other algae.

The ribosomal RNA (rRNA) genes of eukaryotes provide a remarkable example of gene duplication (Cortadas and Pavon, 1982). They may represent as much as 8% of the nuclear genome, as in *Arabidopsis*, for which approximately 570 polycistronic rDNA copies per haploid genome are clustered in two loci on separate chromosomes (Pruitt and Meyerowitz, 1986). The rRNA genes of eukaryotes are organized into a common structure encoding an RNA precursor that is processed into the mature 18s, 5.8S, and 28S rRNAs. Between the three coding regions are internal transcribed spacer regions (ITS-1 and ITS-2), and flanking the operon are the 5' and 3' external transcribed spacer regions (ETS). The operons are then supraorganized into tandem repeating units, separated by non-transcribed DNA known as the intergenic spacer (IGS) (FIG. 1A). IGS's are proposed to reduce silencing of nuclear transgenes due to effects on chromatin structure.

SUMMARY

The embodiments disclosed herein are based, in part, on Applicants' discovery of a novel means for nuclear genetic engineering in algae inovlving double homologous recombination, and allowing site-directed nuclear integration of genes and sequences of interest. Disclosed herein are means for providing constitutive transcription of the genes and/or sequences of interest, e.g. using unique regulatory sequences from an aquatic virus, and/or providing inducible transcription of the genes and/or sequences of interest, e.g. using regulatory sequences that render transcription responsive to the presence of ammonium, nitrate or $CO_2$. The non-random nuclear integration of genes and sequences of interest in the embodiments disclosed herein can occur in unique genomic regions readily accessible for homologous recombination and for active transgene and trans-sequence expression.

Accordingly, some embodiments provide isolated polynucleotide sequences that comprise, consist essentially of, or consist of algal-specific regulatory sequences disclosed herein, including but not limited to algal-specific promoters, 3' untranslated regions (UTR's), (intergenic sequences) IGS's and the like, or functional fragments thereof. Also provided are percent variants of the isolated polynucleotides and fragments thereof, as described in further detail below.

Various embodiments provide, for example, nucleic acids, polypeptides, vectors, expression cassettes, and cells useful for transgenic expression of nucleic acid sequences. In various embodiments, vectors can contain nuclear-based sequences of unicellular photosynthetic bioprocess organisms for the constitutive and/or inducible regulation of endogenous and/or heterologous genes or DNA sequences. The genes may be used, for example, for the production of food- and feed-stuffs, oils, biofuels, starches, raw materials, pharmaceuticals or fine chemicals. The sequences can be used for a protein product or an RNA product. The latter can be useful for RNA interference.

Vectors for gene expression in unicellular bioprocess algae are disclosed in accordance with some embodiments of the present invention. In some embodiments, the vectors comprise an algal-specific promoter. In some embodiments, the algal-specific promoter can be an algal-specific ammonium transporter (AMT1) promoter, an algal-specific AMT2 promoter, an algal-specific AMT4 promoter, an algal-specific nitrate reductase (NIT1) promoter, or an algal-specific $CO_2$ transporter (RH1) promotor. In some embodiments, the unicellular bioprocess algae can be marine algae. In some embodiments, the unicellular bioprocess algae can be freshwater or brackish algae. In some embodiments, the algal-specific promoter can be a promoter specific to an algal species selected from the group consisting of *Dunaliella, Tetraselmis, Chlorella* or *Chlamydomonas*. In some embodiments, the vector comprises a gene of interest operably linked to the algal-specific promoter. In some embodiments, the gene can encode IPP isomerase, acetyl-coA synthetase, pyruvate dehydrogenase, pyruvate decarboxylase, acetaldehyde dehydrogenase, acetyl-coA carboxylase, α-carboxyltransferase, β-carboxyltransferase, biotin carboxylase, biotin carboxyl carrier protein, acyl-ACP thioesterase, 3-ketoacyl-ACP synthetases I, II and III, ATP citrate lyase, carbonic anhydrase, fatty acid desaturases, $CO_2$ transporter Rh1 or acyl CoA diacylglycerol acyltransferase. In some embodiments, the vector further comprises a nucleic acid sequence comprising at least a portion of an intergenic spacer region (IGS) of an rRNA locus. In some embodiments, the vector further comprises a gene of interest operably linked to the algal-specific promoter, wherein the IGS flanks both sides of the algal-specific promoter and the gene of interest.

A unicellular bioprocess alga for gene expression is disclosed in accordance with some embodiments of the present invention. In some embodiments, the unicellular bioprocess alga comprises: a unicellular bioprocess algae transformed with a vector comprising an algal-specific promoter; a gene of interest; an algal-specific terminator; and a nucleic acid sequence comprising an intergenic spacer region of an rRNA locus, wherein the gene of interest is operably linked to said algal-specific promoter.

A method for producing a gene product of interest in an alga is disclosed in accordance with some embodiments of the present invention. In some embodiments, the method comprises transforming an alga with a vector including a gene of interest operably linked to an algal-specific promoter.

BRIEF DESCRIPTION OF THE DRAWINGS

FIGS. 1A-1B. Generic organisation of pol I transcription units. (A) The rRNA coding units are separated by intergenic spacers (IGS). (B) The IGS contains a series of terminators (term), enhancers, a spacer promoter (SP), a proximal terminator (PT), the upstream promoter element (UPE) and the promoter core, which includes the rInr. The sites of transcription initiation are indicated by tis and/or the bent arrows. From: Paule, M. R. et al., *Nucl. Acids Res.* 2000 28:1283-1298.

DETAILED DESCRIPTION

It is preferred to use host-specific nuclear genome flanking and regulatory sequences for each alga of interest for expression of target genes in nuclei of bioprocess algae. In some embodiments, the bioprocess algae can be marine or freshwater algae. Thus, it is desirable to identify contiguous nuclear genome sequences sufficient for designing and executing nuclear genetic engineering for unicellular photosynthetic bioprocess algae. Once these fundamental sequences are discovered, further modifications may be made for purposes of optimized translation for example.

Until now, no endogenous nuclear genome sequences sufficient for designing and executing nuclear genetic engineering have been reported for unicellular photosynthetic bioprocess algae. Further, associated methods for application of such sequences are unreported. Bioprocess algae are those that are scaleable and commercially viable. Four target well-known bioprocess microalgae are *Dunaliella, Tetraselmis, Chlorella* and *Chlamydomonas*. The former is recognized for its use in producing carotenoids and glycerol for fine chemicals, foodstuff additives, and dietary supplements, the latter in aquaculture feed. *Chlamydomonas* has been successfully genetically engineered for large-scale production of medically relevant proteins (reviewed in Franklin, S. E. and Mayfield, S. P., *Expert Opinion in Biological Therapy* 5(2):225-235; 2005). More recently interest in algae biomass for biofuels feedstock and the associated carbon dioxide and nitrous oxide sequestration has emerged (Christi, *Biotechnology Advances* 25: 294-306; 2007; Huntley, M. E. and Redalje, *Mitigation and Adaptation Strategies for Global Change* 12: 573-608; 2007).

Regulating fatty acid or other biosynthetic gene expression with inducible promoters can circumvent the negative effects upon membrane synthesis or algae viability that may result if such biosynthetic gene expression was altered throughout the entire life cycle of the organism. The transcription profile of Rh1 suggests its promoter may be well suited to regulating transgene expression in algae propagated in photobioreactors under nutrient replete conditions.

Ribosomal RNA (rRNA) loci are highly active euchromatic regions of the nuclear genome and have significant utility as facilitators of gene expression in bioprocess algae. Transcription of rRNA is highly regulated to correlate with growth rate (reviewed in Sollner-Webb and Mougey, 1991). The use of algae-specific rDNA sequences in transformation vectors to promote integration into rDNA loci provides the benefit of circumventing gene silencing that can occur with nuclear transformation using viral sequences, which has been observed with the CaMV 35S promoter (Mishiba et al., 2005). Additionally, inclusion of the nontranscribed intergenic spacer region of the rDNA locus in our transformation vectors enhances of nuclear homologous recombination, as reported for *Arabidopsis* where a nine-fold enhancement was observed (Urawa et al., 2001).

In some embodiments, methods are provided for isolation of nuclear DNA sequences from bioprocess algae. As discussed above, until now, no contiguous nuclear genome sequences sufficient for designing and executing nuclear genetic engineering have been reported for unicellular photosynthetic bioprocess algae. In various embodiments, nuclear nucleic acids from unicellular bioprocess algae can be used for identification of contiguous nuclear genome sequences sufficient for designing integrating nuclear DNA constructs, and gene expression cassettes thereof. In some embodiments, methods are provided for obtaining specific sequences of the algal nuclear genome. Also disclosed are nuclear DNA sequences useful for integration into algae nuclei. Exemplary algae include without limitation *Chlorella, Chlamydmonas, Dunaliella* and *Tetraselmis*.

Some embodiments provide expression vectors for the nuclear integration and expression of genes in algae. In various embodiments, methods are provided for transformation of expression vectors into algae. In other embodiments, methods are provided for the expression of genes. In some embodiments, the genes can be, for example, genes that participate in antibiotic resistance. In other embodiments, the genes can be, for example, genes that participate in carbon metabolism, such as fatty acid biosynthesis.

Some Definitions

Unless defined otherwise, all technical and scientific terms used herein have the meaning commonly understood by a person skilled in the art to which this invention belongs. As used herein, the following terms have the meanings ascribed to them unless specified otherwise.

The articles "a" and "an" are used herein to refer to one or to more than one (i.e., to at least one) of the grammatical object of the article. By way of example, "an element" means one element or more than one element.

By "expression vector" is meant a vector that permits the expression of a polynucleotide inside a cell and/or plastid. Expression of a polynucleotide includes transcriptional and/or post-transcriptional events. An "expression construct" is an expression vector into which a nucleotide sequence of interest has been inserted in a manner so as to be positioned to be operably linked to the expression sequences present in the expression vector.

The phrase "expression cassette" refers to a complete unit of gene expression and regulation, including structural genes and regulating nucleic acid sequences recognized by regulator gene products.

By "plasmid" is meant a circular nucleic acid vector. Plasmids contain an origin of replication that allows many copies of the plasmid to be produced in a bacterial (or sometimes eukaryotic) cell without integration of the plasmid into the host cell DNA.

The term "gene" as used herein refers to any and all discrete coding regions of a host genome, or regions that code for a functional RNA only (e.g., tRNA, rRNA, regulatory RNAs such as ribozymes, etc.) as well as associated non-coding regions and optionally regulatory regions. In certain embodiments, the term "gene" includes within its scope the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The gene sequences may be cDNA or genomic DNA or a fragment thereof. The gene may be introduced into an appropriate vector for extrachromosomal maintenance or for integration into the host.

The term "control sequences" or "regulatory sequence" as used herein refers to nucleic acid sequences that control and/or regulate the expression of an operably linked coding sequence in a particular host organism. Control sequences that are suitable for prokaryotes, for example, include a promoter, optionally an operator sequence, and a ribosome binding site. Eukaryotic cells are known to utilize promoters, polyadenylation signals, and enhancers; elements of prokaryotic control sequences are specifically employed in plastids and chloroplasts. The skilled artisan will understand that a "functional fragment" of a sequence is a fragment that is shorter than the reference sequence, but includes all sequences necessary for the desired function. By way of example, a "functional fragment" of a promoter refers to a fragment of a longer promoter sequence that includes the necessary promoter elements to function to direct transcription in vitro and/or in vivo. Similarly, a "functional fragment" of an intergenic spacer sequence (IGS), or 3'UTR sequence, includes all of the sequences necessary to achieve the regulatory or control functions as the full length sequence.

By "operably connected" or "operably linked" and the like is meant a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. In some embodiments, operably linked means that the nucleic acid sequences being linked are typically contiguous and, where necessary to join two protein coding regions, contiguous and in reading frame. A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

"Operably connecting" a promoter to a transcribable polynucleotide means placing the transcribable polynucleotide (e.g., protein encoding polynucleotide or other transcript) under the regulatory control of a promoter, which then controls the transcription and optionally translation of that polynucleotide. In the construction of heterologous promoter/structural gene combinations, it is generally preferred to position a promoter or variant thereof at a distance from the transcription start site of the transcribable polynucleotide, which is approximately the same as the distance between that promoter and the gene it controls in its natural setting; i.e., the gene from which the promoter is derived. As is known in the art, some variation in this distance can be accommodated. Similarly, the preferred positioning of a regulatory sequence element (e.g., an operator, enhancer, etc.) with respect to a transcribable polynucleotide to be placed under its control is typically defined by the positioning of the element in its natural setting; i.e., the genes from which it is derived.

The term "promoter" as used herein refers to a minimal nucleic acid sequence sufficient to direct transcription of a nucleic acid sequence to which it is operably linked. The term "promoter" is also meant to encompass those promoter elements sufficient for promoter-dependent gene expression controllable for cell-type specific expression, tissue-specific expression, or inducible by external signals or agents; such elements may be located in the 5' or 3' regions of the naturally-occurring gene.

The term "inducible promoter" as used herein refers to a promoter that is transcriptionally active when bound to a transcriptional activator, which in turn is activated under a specific condition(s), e.g., in the presence of a particular chemical signal or combination of chemical signals that affect binding of the transcriptional activator, e.g., $CO_2$ or $NO_2$, to the inducible promoter and/or affect function of the transcriptional activator itself The term "construct" as used herein refers to a recombinant nucleotide sequence, generally a recombinant nucleic acid molecule, that has been generated for the purpose of the expression of a specific nucleotide sequence(s), or is to be used in the construction of other recombinant nucleotide sequences. In general, "construct" is used herein to refer to a recombinant nucleic acid molecule.

The term "transformation" as used herein refers to a permanent or transient genetic change, preferably a permanent genetic change, induced in a cell following incorporation of non-host nucleic acid sequences. Where the cell is a plant cell, a permanent genetic change is generally achieved by introduction of the nucleic acid into the genome of the cell, and specifically into the plastome (plastid genome) of the cell for plastid-encoded genetic change.

The term "host cell" as used herein refers to a cell(s) that is to be transformed using the methods and compositions of the invention. Transformation may be designed to non-selectively or selectively transform the target cell(s). In general, host cell as used herein means an algal cell into which a nucleic acid of interest is transformed.

The term "transformed cell" as used herein refers to a cell into which (or into an ancestor of which) has been introduced, by means of recombinant nucleic acid techniques, a nucleic acid molecule encoding a gene product (e.g., RNA and/or protein) of interest (e.g., nucleic acid encoding a cellular product).

The term "gene of interest," "nucleotide sequence of interest" or "nucleic acid of interest" as used herein refers to any nucleotide or nucleic acid sequence that encodes a protein or other molecule that is desirable for expression in a host cell (e.g., for production of the protein or other biological molecule (e.g., an RNA product) in the target cell). The nucleotide sequence of interest is generally operatively linked to other sequences which are needed for its expression, e.g., a promoter. Further, the sequence itself may be regulatory in nature and thus of interest for expression of biologics in the target cell.

"Culturing" signifies incubating a cell or organism under conditions wherein the cell or organism can carry out some, if not all, biological processes. For example, a cell that is cultured may be growing or reproducing, or it may be non-viable but still capable of carrying out biological and/or biochemical processes such as replication, transcription, translation, etc.

By "transgenic organism" is meant a non-human organism (e.g., single-cell organisms (e.g., microalgae), mammal, non-mammal (e.g., nematode or *Drosophila*)) having a non-endogenous (i.e., heterologous) nucleic acid sequence present in a portion of its cells or stably integrated into its germ line nucleic acid.

The term "biomass," as used herein refers to a mass of living or biological material and includes both natural and processed, as well as natural organic materials more broadly.

The invention will now be described in further detail. As will be taught below, sequences in algae can be discovered based on known sequences in other organisms, although other methods for identifying sequences can also be used. Briefly, to clone a desired algae sequence, genomic DNA is prepared from algae, the DNA is sequenced, desired sequences for cloning are identified from analysis of the DNA sequence, probes based on the DNA sequence are designed and prepared, and the desired sequence is amplified. The cloned algae sequence can be used for a variety of purposes, including, for example, regulating expression of genes of interest and as a probe to identify and clone homologous sequences from other organisms.

Preparation of Algae DNA

Total genomic DNA can be prepared from the algae species of choice using a variety of methods known in the art. For example, total genomic DNA can be prepared using the Plant DNAzol™ genomic extraction method (Invitrogen). In some embodiments, the genomic DNA is randomly sheared and ligated into a cloning vector. For example, the DNA can be sheared to an average size of 3 kilobases. The sheared ends of the molecules can be repaired using, for example, T4 DNA polymerase and Klenow DNA polymerase. Subsequently, the repaired ends can be dephosphorylated using, for example, Calf Intestinal Phosphatase (New England Biolabs). The resulting blunt-ended molecules can be ligated into any suitable cloning vector. Preferably, the resulting molecules are ligated into, for example, the TOPO Shotgun cloning vector (Invitrogen™).

The plasmids can then transformed into any suitable bacteria by any of a variety of transformation procedures known in the art. Transformation and selection procedures are described in more detail below. In some embodiments, the plasmids can be transformed into TOP10™ *E. coli* by, for example, heat shock. The transformed bacteria can be plated on a suitable growth medium, such as, for example, LB medium supplemented with 100 ug/ml carbenicillin and x-galactosidase. Colonies are transferred to a suitable membrane, such as, for example, a nylon membrane. The colonies on the membrane are lysed, and the membrane is dessicated and prepared for hybridization. In some embodiments, colonies are transferred to Biodyne B 82 mm nylon membrane disks (Pall Corporation) and prepared for hybridization after colony lysis and dessication.

Synthesis of Nucleic Acid Probes and Identification of Nuclear DNA

In various embodiments, nucleic acid probes to identify clones containing nuclear sequences of interest can be prepared using PCR amplification of a fragment located in a suitable region of the gene of interest. In some embodiments, probes can be prepared by PCR amplification of, for example, a 200 to 500 bp fragment of nucleic acid located within the first exon of the gene of interest. PCR primers can be designed by identifying the coding sequences of highest conservation in an alignment of published sequences for the species and/or its closest known relatives.

In some embodiments, the amplified nucleic acid fragment can be labeled using any suitable labeling means. For example, in some embodiments the amplified nucleic acid fragment can be labeled with biotin using the North2South™ Direct HRP labeling and detection kit (Pierce).

After hybridization of the labeled nucleic acid fragment to colonies on the nylon membranes prepared as described above, the label can be detected. For example, a biotin label can be detected with strepavidin-HRP and a chemiluminescent substrate for HRP according to kit directions. In some embodiments, after a suitable incubation such as, for example, five minutes, the hybridized clones can be detected by imaging the nylon membrane. In some embodiments, a CCD camera of a ChemiDoc Imager (BioRad) can be used for imaging. The resulting image can be used to identify corresponding bacterial colonies on the original plates, and the selected colonies are amplified in, for example, LB broth culture.

In some embodiments, plasmid DNA can be prepared from the bacterial cultures using any suitable method for preparing plasmid DNA known in the art. In some embodiments, plasmid DNA can be prepared using, for example, the Quantum™ Prep Miniprep Kit (BioRad). The plasmid DNA can then sequenced. In embodiments were the PCR fragment was subcloned into TOPO® Shotgun cloning vector, the plasmid DNA can be sequenced, for example, with T7 and T3 primers. Library screening and clone sequencing proceeds until clones are identified containing transcriptional promoter sequences of interest.

Sequencing of Nuclear DNA

Nuclear DNA can be sequenced by a variety of methods known in the art. In some embodiments, nuclear DNA can be sequenced using, for example without limitation, shotgun sequencing or chromosome walking techniques. In various embodiments, shotgun genome sequencing can be performed using, for example, the pCR4 TOPO® blunt shotgun cloning kit according to the manufacturer's instructions (Invitrogen). In various embodiments, shotgun clones can be sequenced from both ends using, for example, T7 and T3 oligonucleotide primers and a KB basecaller integrated with an ABI 3730XL® sequencer (Applied Biosystems, Foster City, Calif.). Sequences can be trimmed to remove the vector sequences and low quality sequences. Nuclear DNA can be sequenced by a number of different methods known in the art for sequencing DNA.

Sequence information obtained from sequencing the DNA can be analyzed using a variety of methods, including, for example, a variety of different software programs. For example, sequences can be processed to identify coding regions using, for example, the Glimmer® software program. ORFs (open reading frames) can be saved, for example, in both nucleotide and amino acid sequence Fasta formats. Any putative ORFs can be searched against the latest Non-redundant (NR) database from NCBI using the BLASTP program to determine similarity to known protein sequences in the database.

PCR Cloning of Algae Sequences

Sequences of interest can be cloned from algae genomic DNA as follows. In some embodiments, sequences can be cloned from a total genomic DNA preparation of *Chlamydomonas*. Sequences of interest include, for example without limitation, inducible promoter sequences, including, for example, promoter sequences for the environmentally regulated genes AMT1, AMT2, AMT4 (ammonium transporter), NIT1 (nitrate reductase), and RH1 ($CO_2$ transporter). Algal sequences can be accessed from publicly available databases, such as the database of the DOE Joint Genome Institute website. As such, the skilled artisan will readily appreciate that the methods described herein are applicable to any sequence of interest and are not limited to the specific genes listed herein.

The positions of transcription initiation and translation initiation for each gene are determined from examination of the sequence. In some embodiments, examination of sequences can be carried out using the software program PromAn (hypertext transfer protocol bips.u-strasbg.fr/Pro-mAn). A segment of genomic sequence extending from, for example, approximately −1000 to +40 base pairs relative to the translation initiation codon can be identified for protein coding genes.

When the desired promoter sequences are identified in clones derived from the shotgun *Chlamydomonas* library, subfragments can be cloned by, for example, PCR amplification (approximately −1000 to +40 for protein coding genes; approximately −200 to +10 for rRNA genes). Primer sets can be designed using a variety of methods known in the art. In some embodiments, primer sets can be designed using, for example, Primer Quest software provided by Integrated DNA Technologies (Coralville, Iowa, U.S.A.), with the addition of unique restriction sites on the ends of the amplified product. PCR amplification can be used to amplify the sequences of interest. In some embodiments, PCR can be performed using, for example, Pfx Accuprime™ DNA Polymerase (Invitrogen™) using conditions that are appropriate for the specific primer set. PCR products are digested with XhoI or other useful restriction enzymes, cleaned using the PCR Purification Kit (Qiagen™) and ligated into the XhoI or other relevant restriction site of a multipurpose cloning vector (examples of which are listed below in the section labeled "Vectors").

The promoter sequences derived from screening a *Chlamydomonas* genomic library as described above can be used for a variety of purposes. In some embodiments, the promoter sequences can be subcloned into the *Chlamydomonas* vector pMF124cGFP (Fuhrmann et al., 1999). This cloning step replaces the vector's rbcS2 promoter with the new promoter of interest. The derivative vector and the parental vector pMF124cGFP are independently transformed into *Chlamydomonas* according to the desired method described below (Transformation and Expression). The functionality of the cloned promoter can be determined by comparison of the number of transformants recovered after transformation with the parental vector pMF124cGFP versus the number of transformants recovered after transformation with the derivative vector containing the newly cloned promoter of interest. The ble selectable marker gene of the parental vector, pMF124cGFP, may be replaced by any other suitable selectable marker in subsequent cloning steps. Such selectable marker genes include, but are not limited to, the phosphinothricin acetyltransferase genes (PAT) or (BAR), conferring resistance to gluphosinate; the chloramphenicol acetyltransferase gene (CAT) conferring resistance to chloramphenicol and the like.

In other embodiments, the cloned promoter sequence can be used as a probe to identify and clone the homologous promoter from an alternative bioprocess algae such as, for example, *Dunaliella*, *Tetraselmis* or *Chlorella*. As described above for *Chlamydomonas*, a genomic library is constructed and screened for the desired algae species. The desired promoter sequences can be subcloned into a multipurpose cloning vector for future transformation vector development.

After functionality of the desired regulatory promoter sequence is determined, genes of interest are added to the derivative vector immediately downstream of the cloned promoter sequence. The natural 3'UTR of the gene of interest is included in the new vector to effectively regulate transcript stability and expression of the desired gene. Desirable genes include, but are not limited to, fatty acid synthases (Bonaventure et al., 2003; Wu et al., 1994), desaturases (Pidkowich et al., 2007) or the rate-limiting step for total output, accD (reviewed in Rawsthorne, 2002). Also included are any of the genes, such as listed in Provisional Patent Application No. 60/971,846, which is incorporated herein by reference in its entirety, with the modification of such genes, when appropriate to target the gene product to the chloroplast, by the inclusion of a chloroplast targeting peptide sequence derived from the host algae at the 5' end of the gene. Also included are homologues of the above mentioned genes cloned from a genomic library of the desired bioprocess algae. Also included are complementary DNA sequences for the above mentioned genes, but not limited to those genes listed above, that facilitate antisense, hairpin, or siRNA transcripts that silence translation of target genes in transformed bioprocess algae.

Vectors

Some of the presently disclosed embodiments are directed to nuclear DNA vectors for targeted integration into the nuclear genome. For example, in some embodiments, the vectors can be used to target integration of a nucleic acid to a particular location of the host genome. In various embodiments, the nuclear DNA vectors comprise nuclear DNA sequences capable of targeting integration into the nuclear genome. In some embodiments, the nuclear DNA vectors further comprise a gene of interest to be integrated into the nuclear genome and expressed by the algae. In some embodiments, the vectors comprise gene expression cassettes. In various embodiments, the gene expression cassettes comprise a gene of interest, expressed in greater detail below, to be integrated into the nuclear genome. Standard molecular biology techniques known to those skilled in the art of recombinant DNA and cloning can be applied to carry out the methods unless otherwise specified. For example, the various fragments comprising the various constructs, expression cassettes, markers, and the like may be introduced consecutively by restriction enzyme cleavage of an appropriate replication system, and insertion of the particular construct or fragment into the available site. After ligation and cloning the vector may be isolated for further manipulation. All of these techniques are amply exemplified in the literature and find particular exemplification in Maniatis et al., Molecular cloning: a laboratory manual, $3^{rd}$ ed. (2001) Cold Spring Harbor Laboratory Press, Cold Spring Harbor, N.Y.

In developing the constructs the various fragments comprising the regulatory regions and open reading frame may be subjected to different processing conditions, such as ligation, restriction enzyme digestion, PCR, in vitro mutagenesis, linkers and adapters addition, and the like. Thus, nucleotide transitions, transversions, insertions, deletions, or the like, may be performed on the DNA which is employed in the regulatory regions or the DNA sequences of interest for expression in the plastids. Methods for restriction digests, Klenow blunt end treatments, ligations, and the like are well known to those in the art and are described, for example, by Maniatis et al.

During the preparation of the constructs, the various fragments of DNA can be cloned in an appropriate cloning vector, which allows for amplification of the DNA, modification of the DNA or manipulation of the DNA by joining or removing sequences, linkers, or the like. In some embodiments, the vectors will be capable of replication to at least a relatively high copy number in *E. coli*. A number of vectors are readily available for cloning, including such vectors as pBR322, vectors of the pUC series, the M13 series vectors, and pBluescript vectors (Stratagene; La Jolla, Calif.).

A genomic DNA segment for targeted integration can be from about ten nucleotides to about 20,000 nucleotides long. In some embodiments, a genomic DNA segment for targeted integration can be about can be from about 1,000 to about 10,000 nucleotides long. In other embodiments, a genomic DNA segment for targeted integration is between about 1 kb to about 2 kb long. In some embodiments, a "contiguous" piece of nuclear genomic DNA can be split into two flanking pieces when the genes of interest are cloned into the non-coding region of the contiguous DNA. In other embodiments, the flanking pieces can comprise segments of nuclear DNA sequence which are not contiguous with one another. In some embodiments, a first flanking genomic DNA segment is located between about 0 to about 10,000 base pairs away from a second flanking genomic DNA segment in the nuclear genome. In a preferred embodiment, the flanking genomic DNA segment can be derived from, for example, the Intergenic Spacer Region of the 18s rDNA operon.

The DNA of interest can vary. In some embodiments, the DNA of interest can comprise, for example without limitation, a selectable marker gene and at least one gene of interest. Various examples of genes of interest are described in more detail below.

The DNA segments can then be introduced into a vector to generate a backbone expression vector for targeted integration of a foreign gene into the nuclear genome. Any of a variety of methods known in the art for introducing DNA sequences can be used. For example, DNA segments can be amplified from isolated nuclear genomic DNA using appropriate primers and PCR. The amplified products can then be introduced into any of a variety of suitable cloning vectors by, for example, ligation. Some useful vectors include, for example without limitation, pGEM13z, pGEMT and pGEMTEasy (Promega, Madison, Wis.); pSTBlue1 (EMD Chemicals Inc. San Diego, Calif.); and pcDNA3.1, pCR4-TOPO, pCR-TOPO-II, pCRBlunt-II-TOPO (Invitrogen, Carlsbad, Calif.). In some embodiments, at least one DNA segment from a nucleus is introduced into a vector. In other embodiments, two or more DNA segments from a nucleus are introduced into a vector. In some embodiments, the two DNA segments can be adjacent to one another in the vector. In some embodiments, the two DNA segments introduced into a vector can be separated by, for example, between about one and thirty base pairs. In some embodiments, the sequences separating the two DNA segments can contain at least one restriction endonuclease recognition site.

In various embodiments, regulatory sequences can be included in the vectors of the present invention. In some embodiments, the regulatory sequences comprise nucleic acid sequences for regulating expression of genes (e.g., a DNA or nucleic acid of interest) introduced into the nuclear genome. In various embodiments, the regulatory sequences can be introduced into a backbone expression vector. For example, various regulatory sequences can be identified from the algal nuclear genome. The regulatory sequences can comprise, for example, a promoter, an enhancer, an intron, an exon, a 5' UTR, a 3'UTR, or any portions thereof, or any combination of any of the foregoing, of a nuclear gene. Using standard molecular biology techniques, the regulatory sequences can be introduced into the desired vector. In some embodiments, the vectors comprise a cloning vector or a vector comprising DNA segments for targeted integration. Recognition sequences for restriction enzymes can be engineered to be present adjacent to the ends of the regulatory sequences. The recognition sequences for restriction enzymes can be used to facilitate introduction of the regulatory sequence into the vector.

In some embodiments, the regulatory sequence or sequences, e.g. the 5'UTR, 3' UTR, or the like, can include up to about 1,000 bases upstream of a transcript initiation site as a transcriptional promoter, and can include, for example, sequences located between the transcript initiation site and a translation start codon, ATG. In some embodiments, up to about 1,000 bases upstream of the transcript initiation site (e.g., 100, 200, 300, 400, 500, 600, 700, 800, 900, 1,000, or more, or any number of bases in between) can be used as a transcriptional promoter. In some embodiments, the promoter can include up to about 10 to about 1,000 bases upstream of a transcript initiation site. In some embodiments, the 5' UTR regulatory sequence can include sequences located between a transcript initiation site up to the translation start codon, ATG.

In some embodiments, the regulatory sequence, or sequences, can be derived from the Nitrate Reductase (Nit1), Ammonium Transporter (AMT1, AMT2, or AMT4), or $CO_2$ transporter Rh1 genes, or homologues thereof, from algae, e.g from *Chlamydomonas reinhardtii* or the like. By way of the example, in some embodiments, the regulatory sequence can include the Nit1 promoter from *Chlamydomonas reinhardtii*, e.g. a sequence comprising, SEQ ID NO:1, or a functional fragment thereof. In some embodiments, the regulatory sequence can be derived from the Ammonium Transporter promoter of *Chlamydomonas reinhardtii* (AMT1). For example, in some embodiments, the regulatory sequence can include the promoter, 3'UTR, and/or other regulatory sequence from *Chlamydomonas* AMT1. In some embodiments, the AMT1 regulatory sequence includes the sequence shown in SEQ ID NO: 2, or a functional fragment thereof. The sequence segment 3'-CTCTGACCTAAGT-TAAAATAGACACAAACATG-5' (SEQ ID NO: 4) includes the transcription start "C", the Shine Dalgarno region and the translation start codon ATG of the AMT1 gene. In some embodiments, the regulatory sequence can include the AMT1 3'UTR shown in SEQ ID NO: 18, or a functional fragment thereof. In some embodiments, the regulatory sequence can include the AMT2 promoter as shown in SEQ ID NO: 19, or a functional fragment thereof. In some embodiments, the regulatory sequence can include the AMT2 3'UTR shown in SEQ ID NO: 20, or a functional fragment thereof. In some embodiments, the regulatory sequence can include the AMT4 promoter as shown in SEQ ID NO: 21, or a functional fragment thereof. In some embodiments, the regulatory sequence can include the AMT4 3'UTR shown in SEQ ID NO: 22, or a functional fragment thereof. In some embodiments, the Rh1 gene has the sequence shown in SEQ ID NO: 5. The Rh1 sequence can comprise 5'-CGGAACTCAGGCCGGCAACCATG-3' (SEQ ID NO: 7), which includes the transcription start "C" and the translation start codon ATG. The protein sequence of *Chlamydomonas reinhardtii* Rh1 protein is shown in SEQ ID NO: 8. In some embodiments, the regulatory sequence can include the Rh1 promoter as shown in SEQ ID NO: 23, or a functional fragment thereof. In some embodiments, the regulatory sequence can include the Rh1 3'UTR shown in SEQ ID NO: 24, or a functional fragment thereof. In some embodiments, the regulatory sequence can include a sequence derived from the VP54 gene from *Paramecium bursarium Chlorella* virus 1 (PBCV-1), or the like. For example, in some embodiments, the regulatory sequence can include the sequence shown in SEQ ID NO: 7. In some embodiments, the regulatory sequence can include an IGS, e.g. an IGS from *Chlamydamonas* such as SEQ ID NO: 11, or a functional fragement thereof, or an IGS from *Chlorella*, such as SEQ ID NO: 14, or a functional fragment thereof.

In accordance with the disclosure herein, some embodiments provide isolated polynucleotide sequences that are percent variants, that comprise, consist essentially of, or consist of sequences that are 80%, 85%, 86%, 87%, 88%, 89%, 90%, 91%, 92%, 93%, 95%, 95%, 96%, 97%, 98%, 99% or more, identical, to the regulatory sequences disclosed herein. Some embodiments relate to isolated polynucleotides that comprise, consist essentially of, or consist of sequences that are 80%, 85%, 86%, 87%, 88%, 89%, 90%, 91%, 92%, 93%, 95%, 95%, 96%, 97%, 98%, 99% or more, identical, to the functional fragments of the regulatory sequences described herein, e.g. CAAT boxes, TFII-A binding sites, TFII-I binding sites, and the like, as described herein. The percent identity between two sequences can be determined using publicly available algorithms, such as BLAST™ sequence analysis software, and the like. Preferably, the percent variants disclosed herein retain their regulatory function, e.g. ad promoters, 3'UTR regulatory sequences, IGSs and the like.

The skilled artisan will readily appreciate that the "regulatory" sequences disclosed herein can include any combination of the regulatory elements or functional fragments described herein, e.g. an AMT1 promoter, and AMT2 3'UTR, and an IGS from an alagae such as *Chlamydamonas, Dunaliella, Tetraselmis, Chlorella*, or the like.

In some embodiments, the 3' UTR is derived from the gene of interest being cloned into the expression vector such as, for example, the gene encoding an IPP isomerase, acetyl-coA synthetase, pyruvate dehydrogenase, pyruvate decarboxylase, acetaldehyde dehydrogenase, acetyl-coA carboxylase, α-carboxyltransferase, β-carboxyltransferase, biotin carboxylase, biotin carboxyl carrier protein, acyl-ACP thioesterase, 3-ketoacyl-ACP synthetase I, II or III, ATP citrate lyase, carbonic anhydrase, fatty acid desaturase or acyl-CoA diacylglycerol acyltransferase. In other embodiments, the 3' UTR is derived from the gene contributing the inducible promoter, for example AMT1; 1, (SEQ ID NO:18) AMT2 (SEQ ID NO:20), AMT4 (SEQ ID NO:22), or Rh1 (SEQ ID NO:24) or functional fragments thereof. The 3'UTR is defined as the sequences necessary for terminating transcription of the gene cassette and stabilizing the transcript, including, but not limited to the polyadenylation signal.

In some embodiments, nucleic acid sequences for regulating expression of genes introduced into the nuclear genome can be introduced into a vector by PCR amplification of a 5'UTR, 3' UTR, a promoter and/or an enhancer, or portion thereof, one or more nuclear genes. Using suitable PCR cycling conditions, primers flanking the sequences to be amplified are used to amplify the regulatory sequences. In some embodiments, the primers can include recognition sequences for any of a variety of restriction enzymes, thereby introducing those recognition sequences into the PCR amplification products. The PCR product can be digested with the appropriate restriction enzymes and introduced into the corresponding sites of a vector.

In some embodiments, selection of transgenic algae can be facilitated by resistance to antibiotics. Thus, in some embodiments, the vectors can comprise at least one antibiotic resistance gene. The antibiotic resistance gene can be any gene encoding resistance to any antibiotic, including without limitation, spectinomycin, kanamycin, chloramphenicol phleomycin and any analogues.

In some embodiments, the nuclear DNA vectors comprise a gene expression cassette comprising a gene of interest and a promoter identified as described herein, described in more detail below. In some embodiments, the gene of interest can be operably linked to a promoter. In some embodiments, the gene of interest or sequence complementary to the gene of interest can be operably linked to an algal-specific promoter. In some embodiments, the algal-specific promoter is an inducible promoter. In some embodiments, the algal-specific promoter is a constitutive promoter. Promoters that can be used include, for example without limitation, a NIT1 promoter (SEQ ID NO:1), an AMT1 promoter (SEQ ID NO:2), an AMT2 promoter (SEQ ID NO:19), an AMT4 promoter (SEQ ID NO:21) a RH1 promoter (SEQ ID NO:23), a cauliflower mosaic virus 35S promoter, a tobacco mosaic virus promoter, a simian virus 40 promoter, a ubiquitin promoter, a PBCV-1 VP54 promoter (SEQ ID NO:17), or functional fragments thereof, or any other suitable promoter sequence known to those skilled in the art.

In some embodiments, the vectors disclosed herein can include more than one algal-specific promoter. For example, in some embodiments, the vectors disclosed herein can include more than one algal specific promoter that are each operably linked to a gene of interest or a sequence complementary to a gene of interest. In some embodiments, some, but not all of the algal-specific promoters in the vectors disclosed herein can be operably linked to a gene of interest or sequence of interest. By way of example, a vector can include a first gene of interest that is operably linked to a first promoter, e.g. a constitutive or inducible algal-specific promoter, and second gene of interest that is operably linked to a second promoter, e.g. a constitutive or inducible promoter that is the same or different than the first promoter.

In some embodiments, the vectors described herein can include more than one terminator sequence. In some embodiments, each of the terminators can be operably linked to a gene or sequence of interest. In some embodiments, some but not all of the terminators in the vectors disclosed herein are operably linked to a gene of interest or sequence of interest.

In some embodiments, the gene expression cassette can be present in the nuclear DNA vector adjacent to one or more nuclear DNA sequence segments useful for integration into the nuclear genome. In some embodiments, the gene expression cassette can be present in the nuclear DNA vector between two nuclear DNA sequence segments. In a preferred embodiment, the flanking genomic DNA segment is derived from the Intergenic Spacer Region of the 18s rDNA operon.

Transformation and Expression

In various embodiments, the nuclear DNA vectors can be introduced, or transformed, into algae nuclei or other organelles. Genetic engineering techniques known to those skilled in the art of transformation can be applied to carry out the methods using baseline principles and protocols unless otherwise specified.

A variety of different kinds of algae can be used as hosts for transformation with the vectors disclosed herein. In some embodiments, the algae can be *Dunaliella* or *Tetraselmis*. In other embodiments, other algae which can be used may include, for example without limitation, one or more algae selected from *Amphora, Anabaena, Anikstrodesmis, Botryococcus, Chaetoceros, Chlorella, Chlorococcum, Cyclotella, Cylindrotheca, Emiliana, Euglena, Hematococcus, Isochrysis, Monochrysis, Monoraphidium, Nannochloris, Nannnochloropsis, Navicula, Nephrochloris, Nephroselmis, Nitzschia, Nodularia, Nostoc, Oochromonas, Oocystis, Oscillartoria, Pavlova, Phaeodactylum, Playtmonas, Pleurochrysis, Porhyra, Pseudoanabaena, Pyramimonas, Stichococcus, Synechococcus, Synechocystis, Thalassiosira,* and *Trichodesmium*.

A variety of different methods are known for the introduction of DNA into host cell nuclei or chloroplasts. In various embodiments, the vectors can be introduced into algae nuclei by, for example without limitation, electroporation, particle inflow gun bombardment, or magnetophoresis. The latter is a nucleic acid introduction technology using the processes of magnetophoresis and nanotechnology fabrication of micro-sized linear magnets (Kuehnle et al., U.S. Pat. No. 6,706,394; 2004; Kuehnle et al., U.S. Pat. No. 5,516,670; 1996) that proved amenable to effective chloroplast engineering in freshwater *Chlamydomonas*, improving plastid transformation efficiency by two orders of magnitude over the state-of the-art of biolistics (Champagne et al., Magnetophoresis for pathway engineering in green cells. Metabolic engineering V: Genome to Product, Engineering Conferences International Lake Tahoe Calif., Abstracts pp 76; 2004). This technology is described for the first time being applied to saltwater microalgae. Specific examples illustrated use of a variety of different transformation procedures are provided in Examples 15-17 below. Polyethylene glycol treatment of protoplasts is another technique that can be used to transform cells (Maliga, P. Plastid Transformation in Higher Plants. Annu. Rev. Plant Biol. 55:294; 2004).

In various embodiments, the transformation methods can be coupled with one or more methods for visualization or quantification of nucleic acid introduction to one or more algae. Further, it is taught that this can be coupled with identification of any line showing a statistical difference in, for example, growth, fluorescence, carbon metabolism, isoprenoid flux, or fatty acid content from the unaltered phenotype. The transformation methods can also be coupled with visualization or quantification of a product resulting from expression of the introduced nucleic acid.

Transformation into Algae and Selection of Transgenic Lines:

Wild-type algae cells are cultured in an appropriate medium under appropriate light conditions to a midlog phase density of, for example, about $1\text{-}4\times10^6$ cells/mL. Cells can be transformed with any suitable transformation known in the art. In some embodiments, cells can be transformed using either electroporation (EP) (Shimogawara et al., 1998) or biolistic introduction of DNA-coated gold particles (Seashell Technologies) using the particle inflow gun (PIG) (Finer et al., 1992). Cells are allowed to recover in, for example, nonselective liquid medium (EP) or on nylon membranes on agar plates (PIG) for about 24 to about 50 hours. In some embodiments, illumination of, for example, 40 to 80 $\mu E\ m^{-2}\ s^{-1}$ is applied during recovery.

In some embodiments, cells transformed with vector conferring selective resistance to an agent can be selected by transfer of nylon membranes to, for example, agar containing the appropriate selective agent. Electroporated liquid cultures can be collected by centrifugation and plated on agar containing the selective agent. A variety of different algae-specific vectors can be transformed into algae cells. In some embodiments, the vectors comprise a promoter. Transformants can be analyzed as described herein.

In some embodiments, wild-type *Chlamydomonas* or other algae cells can be cultured in TAP or HSA medium under moderate light of 40-80 µE m$^{-2}$ s$^{-1}$ to a midlog phase density of 1-4×10$^6$ cells/mL; *Chlorella* and *Tetraselmis* can similarly be cultured in ASW or F medium; *Dunaliella* can be similarly cultured in 1M NaCl Melis medium. Cells can be transformed, for example, with either of two methods: electroporation (EP) (Shimogawara et al., 1998) or biolistic introduction of DNA-coated gold particles (Seashell Technologies) using the particle inflow gun (PIG) (Finer et al., 1992) or the Bio-Rad Biolistic PDS-1000/He Particle Delivery System (Bio-Rad Laboratories, Hercules, Calif.). Cells are allowed to recover in nonselective liquid medium (EP) or on nylon membranes on agar plates (PIG or Bio-Rad) for 48 hours with illumination of 40 to 80 µE m$^{-2}$ s$^{-1}$.

In some embodiments, algae cells transformed using particle bombardment with control vector pMF124cGFP or derived vectors containing alternative promoters are selected by transfer of nylon membranes to appropriate medium with 2% agar and 15 ug/mL phleomycin (Sigma) or 20 ug/mL zeomycin (Cayla-France). Electroporated liquid cultures are collected by centrifugation and plated at a density of 1×10$^7$ cells on appropriate agar medium with 15 ug/mL phleomycin or 20 ug/mL zeomycin. Phleomycin-resistant transformants appear after 10-14 days.

In some embodiments, transformation of *Chlamydomonas, Chlorella, Dunaliella, Tetraselmis* or other algae with the Rh1 promoter can be performed by particle bombardment or electroporation and recovery for 48 hours in appropriate medium supplemented with 3% CO$_2$ (v/v). Examples of appropriate media for *Chlamydomonas* are TAP or HSA; appropriate medium for *Dunaliella* is 1 M NaCl Melis; appropriate media for *Tetraselmis* or *Chlorella* are ASW or F media. Selection of transformants can be accomplished by addition of 15 ug/mL phleomycin or 20 ug/mL zeomycin to liquid medium and continued CO$_2$ supplementation for 14 days. Individual transformants are recovered by centrifugation and plating on nonselective appropriate medium plus 15 ug/mL phleomycin or 20 ug/mL zeomycin. Phleomycin-resistant transformants appear after 10-14 days.

In some embodiments, transformation of *Chlamydomonas, Chlorella, Dunaliella, Tetraselmis* or other algae with the Nit1 promoter is accomplished by electroporation and recovery for 48 hours in appropriate medium supplemented with 3% CO$_2$ (v/v). Selection of transformants is performed by centrifugation and washing cells twice with 75 mM potassium phosphate buffer pH 7.5, followed by transfer to appropriate minimal medium —NH$_4$Cl, +4 mM KNO$_3$. Phleomycin 15 ug/mL or zeomycin 20 ug/mL is added to the culture after 24 hours of induction by KNO$_3$. Individual transformants are recovered by centrifugation and plating on nonselective appropriate medium or on appropriate medium plus 15 ug/mL phleomycin or 20 ug/mL zeomycin.

In some embodiments, transformation of *Chlamydomonas, Chlorella, Dunaliella, Tetraselmis* or other algae with the AMT promoter is achieved by electroporation or particle bombardment and recovery for 48 hours in TAP medium supplemented with 3% CO$_2$ (v/v). Selection of transformants is performed by centrifugation and washing cells twice with 75 mM potassium phosphate buffer pH 7.5, followed by transfer to TAP minimal medium lacking nitrogen.

Genes for Expression

A wide variety of genes can be introduced into the vectors described above for transformation and expression by the nuclear genome of algae. Illustrative genes can include, without limitation, genes that encode a selectable marker, including, for example, genes that participate in antibiotic resistance. Other illustrative genes include genes that participate in carbon metabolism, such as in isoprenoid and fatty acid biosynthesis. In some embodiments, the genes include, without limitation: IPP isomerase, acetyl-coA synthetase, pyruvate dehydrogenase, pyruvate decarboxylase, acetaldehyde dehydrogenase, acetyl-coA carboxylase, α-carboxyltransferase, β-carboxyltransferase, biotin carboxylase, biotin carboxyl carrier protein, acyl-ACP thioesterase, 3-ketoacyl-ACP synthetases I, II and III, ATP citrate lyase, carbonic anhydrase, fatty acid desaturases, RH1 CO$_2$ transporters and/or acyl-CoA diacylglycerol acyltransferase. Yet other illustrative genes include, without limitation: beta acyl-CoA diacylglycerol acyltransferase 1 (DGAT1) (gi:41387496), ketoacyl ACP synthase (KAS); isopentenyl pyrophosphate isomerase (IPPI); acetyl-coA carboxylase, specifically one or more of its heteromeric subunits: biotin carboxylase (BC), biotin carboxyl carrier protein (BCCP), α-carboxyltransferase (α-CT), β-carboxyltransferase (β-CT), acyl-ACP thioesterase; FatB genes such as, for example, *Arabidopsis thaliana* FATB NM_100724; California Bay Tree thioesterase M94159; *Cuphea hookeriana* 8:0- and 10:0-ACP specific thioesterase (FatB2) U39834; *Cinnamomum camphora* acyl-ACP thioesterase U31813; *Diploknema butyracea* chloroplast palmitoyl/oleoyl specific acyl-acyl carrier protein thioesterase (FatB) AY835984; *Madhuca longifolia* chloroplast stearoyl/oleoyl specific acyl-acyl carrier protein thioesterase precursor (FatB) AY835985; *Populus tomentosa* FATB DQ321500; and *Umbellularia californica* Uc FatB2 UCU17097; acetyl-coA synthetase (ACS) such as, for example, *Arabidopsis* ACS9 gene GI:20805879; *Brassica napus* ACS gene GI:12049721; *Oryza sativa* ACS gene GI:115487538; or *Trifolium pratense* ACS gene GI:84468274; genes that participate in fatty acid biosynthesis via the pyruvate dehydrogenase complex, including without limitation one or more of the following subunits that comprise the complex: Pyruvate dehydrogenase E1α, Pyruvate dehydrogenase E1β, dihydrolipoamide acetyltransferase, and dihydrolipoamide dehydrogenase; and pyruvate decarboxylase.

In various embodiments, transformed algae may be grown in culture to express the genes of interest. After culturing, the gene products can be collected. For increased biomass production, the algal culture amounts can be scaled up to, for example, between about 1 L to about 10,000 L of culture. Culture can be under conditions that are suited for phototrophic, mixotrophic and heterotrophic algae. One possible method for growing transformed algae for expressing genes of interest is described in the Examples below.

The following examples are provided to describe the invention in further detail. These examples serve as illustrations and are not intended to limit the invention. While *Dunaliella* and *Tetraselmis* are exemplified, the nucleic acids, DNA vectors and methods described herein can be applied or adapted to other types of Chlorophyte algae, as well as other algae, as described in greater detail in the sections and subsequent examples below.

EXAMPLE 1

Use of vectors containing antibiotic-resistance genes as described in the Examples allow growth of algae on various antibiotics of varying concentrations as one means for monitoring nucleic acid introduction into host species of interest. This may also be used for gene-function analysis, for monitoring other payload introduction in trans or unlinked to the antibiotic-resistance genes, but is not limited to these applications. Cells are grown in moderate light (80 µE/m$^2$/sec) to a log-phase density of 1×10$^6$ cells/mL in appropriate seawater medium for plating. Transgenic antibiotic- or herbicide-resistant colonies appear dark green; the negative control is colorless and growth-inhibited after 21 days, preferably after 12 days, and more preferably after 10 days on liquid or solidified medium. Resistant colonies are re-cultured on selective medium for one or more months to obtain homogenicity and are maintained under the same or other conditions. Cell growth monitored in liquid culture employs culture tubes, horizontal culture flasks or multi-well culture plates.

A screening process for transgenic *Dunaliella* spp is described using plating methods as in the below Examples. For chloramphenicol selection of *D. salina* using liquid medium, cells at plating densities of 0.5 to 1×10$^6$ cells/mL are inhibited by Day 10 in 200 ug/mL chloramphenicol and greater, based on counts of viable cells. Plating densities of 1.9×10$^6$ cells/mL are inhibited by Day 10 in 600 ug/mL chloramphenicol and greater, and by 500 ug/mL chloramphenicol and greater by Day 14. Recommended levels for selection when plated on solidified medium at 2×10$^5$ cells per 6-cm dish with 0.1% top agar is 700 ug/mL chloramphenicol for both *D. salina* and *D. tertiolecta*. For cells that have been subject to electroporation, 600 ug/mL chloramphenicol is the kill point for *D. salina* plated at 8×10$^5$ cells per 6-cm dish.

*Dunaliella* is very sensitive to the herbicide gluphosinate as selection agent in liquid medium based on replicated platings at 1×10$^6$ cells/mL. Concentrations of 5 ug/mL gluphosinate and greater inhibit cell growth of *Dunaliella* almost immediately. *D. tertiolecta* shows inhibition of cell growth by Day 14 from 2 ug/mL gluphosinate and greater. Recommended levels for selection when plated on solidified medium at 2×10$^5$ cells per 6-cm dish with 0.1% top agar is 14 ug/mL and 16 ug/mL gluphosinate for *D. salina* and *D. tertiolecta*, respectively.

A screening process for transgenic *Tetraselmis* spp is described based on replicated platings. Log phase cultures are concentrated by centrifugation of 700 mL at 2844×g to achieve 8×10$^6$ cells/mL when resuspended in 35 mL or similar of culture medium. Media are either 100% ASW (from Brown L. Production of axenic cultures of algae by an osmotic method. Phycologia 21: 408-410; 1982) modified by using F/2 vitamins, or F/2 35psu-Si media (Guillard, R. R. L. and Ryther, J. H. Studies of marine planktonic diatoms. I. *Cyclotella* nana Hustedt and Detonula confervacea Cleve. Can. J. Microbiol. 8: 229-239; 1962). Both media are at 35 psu for 3.5% NaCl. For preparation of medium solidified with 0.75% agar, 4.5 g of Difco Bacto Agar is autoclaved in 1 L bottles. To this is added 600 mL of sterile media, which is heated until the agar goes into solution. 10 mL of agar with calculated amounts of antibiotics are used in 6 cm culture dishes. A 0.2% top agar for plating of algae cells is prepared by adding 0.5 g of Difco Bacto Agar to 250 mL of either 100% ASW and F/2 35psu-Si media. The agar is used at 38° C. for plating of cells in a 1:1 top-agar: concentrated cells mix, with generally 1 mL per plate. Cultures are incubated at room temperature (20° C.-30° C. avg. 25° C.), 22 uM/m$^2$ sec light intensity with a photoperiod of 14 hr days/10 hr nights. Liquid cultures are further exemplified by use of 5 mL of concentrated culture mixed with calculated amounts of antibiotic in test tubes, with incubation in vertical racks at room temperature (20° C.-30° C. average 25° C.), 22 uM/m$^2$ sec light intensity with a photoperiod of 14 hours. Growth is assessed visually at Day 10.

Results on solidified medium show that less than 100 mg/L chloramphenicol is required to inhibit *Tetraselmis* at this plating density in either 100% ASW or F/2 35psu-Si media. Further, greater than 1000 mg/L kanamycin is required and thus this antibiotic is undesirable for *Tetraselmis* at typical plating densities. The herbicide gluphosinate is toxic to *Tetraselmis* at 15 mg/L by Day 7, but re-growth is observed by Day 15 and thus is not preferred as selection agent in solidified medium. For liquid medium, results from hemocytometer counts of viable cells show that *Tetraselmis* cells undergo three divisions in 7 days in both media at these culture conditions. In contrast, during Day 0 to Day 7, cells in 2.5 mg/L up to 20 mg/L gluphosinate show a decrease in viability from 31% up to 60% in F/2, and 52% up to 84% in 100% ASW medium, respectively. During Day 7 to Day 15, cells in 100% ASW undergo a first doubling in 2.5, 5.0 and 10.0 mg/L gluphosinate, but remain inhibited in 15 and 20 mg/L gluphosinate. By Day 21, cell density has almost doubled in 15 mg/L gluphosinate, but not at 20 mg/L gluphosinate, suggesting that both 15 and 20 mg/L gluphosinate can be used for two-week selection, and that 20 mg/L gluphosinate should be used for three-week selection in 100% ASW. During Day 7 to Day 15 in F/2 liquid medium, cell death is at 87% and 91% at 15 and 20 mg/L gluphosinate, respectively. Some re-growth to initial inoculum levels is seen by Day 21 in 15 mg/L gluphosinate in F/2 liquid, but complete death results by Day 21 in 20 mg/L gluphosinate, suggesting that both 15 and 20 mg/L gluphosinate can be used for two-week selection in F/2 liquid, and that 20 mg/L gluphosinate should be used for three-week selection in F/2 medium. Using this general strategy, additional transformed *Dunaliella* and *Tetraselmis* algae may be generated

EXAMPLE 2

Cloning of Ribosomal DNA Intergenic Spacer (IGS) DNA for Construction of Algae Nuclear Vectors This example illustrates the construction of a baseline vector for nuclear integration and expression of genes of interest or sequences complementary to genes of interest.

Sequence alignment of publicly available sequences of the 18s and 28s rDNA of algal species is performed to design PCR primers. In one example, a forward primer having a target binding sequence of 5'-ctaaaggatgttgacacaatgt-gatttctgc-3' (SEQ ID NO: 9) and a reverse primer having a target binding sequence 5'-ccttggatgtggtagccatctctcatgctc-3' (SEQ ID NO: 10) are used to amplify an IGS of the algae *Chlamydomonas*. Restriction enzyme recognition sites are engineered at the 5' ends of the forward and reverse primers to facilitate subsequent cloning into a multicloning vector. Non-limiting examples of restriction enzyme sequences which can be engineered into the *Chlamydomonas* IGS PCR primers include: BamHI, EcoRI, HindIII, NotI, PmeI, XbaI and XhoI. The target binding regions of the primers hybridize to the 28s and 18s rDNA, respectively and produce a 4 kbp amplification product (SEQ ID NO: 11) that corresponds to positions 403992 through 4036991 of *Chlamydomonas* chromosome 14.

The amplification product is sequenced to confirm its fidelity, and the resulting product is cloned into a standard multipurpose cloning vector by digestion of the amplification product and multipurpose cloning vector, followed by a ligation reaction. The multipurpose cloning vector with the IGS insert is used as a baseline *Chlamydomonas* vector.

In another example, a forward primer having a target binding sequence of 5'-CGACTGAACGCCTCTAAGTCA-GAA-3' (SEQ ID NO: 12) and a reverse primer having a target binding sequence 5'-GCCTGCTTT-GAACACTCTAATTTAC-3' (SEQ ID NO: 13) are used to amplify an IGS of the algae *Chlorella*. Restriction enzyme recognition sites are engineered at the 5' ends of the forward and reverse primers to facilitate subsequent cloning into a multicloning vector. The target binding regions of the primers hybridize to the 28s and 18s rDNA, respectively and produce a 5.78 kbp amplification product (SEQ ID NO: 14).

The amplification product is sequenced to confirm its fidelity, and the resulting product is cloned into a standard multipurpose cloning vector by digestion of the amplification product restriction enzyme recognition sequences in the PCR primers and ligation into the cognate site(s) within the multipurpose cloning vector. The multipurpose cloning vector with the IGS insert is used as a baseline *Chlorella* vector.

After an IGS baseline vector is constructed for a given species of bioprocess algae, a multiple cloning site is inserted into a unique restriction site within the IGS insert within the baseline vector. The enzymes BglI, BpuEI, BstAPI, EcoNI, or SfiI may be used to cut the *Chlamydomonas* PCR product to insert a multicloning site. The unique restriction site for insertion of a multicloning site is positioned such that a minimum of 1 kilobase of IGS DNA is located on either side of the restriction site. The multicloning sites inserted within the IGS sequence are contiguous DNA sequences that include recognition sites for restriction enzymes that are absent from the remainder of the IGS DNA. Examples of sequences that are used to construct a multicloning site within the *Chlamydomonas* IGS include, but are not limited to: ApaLI, AvrII, BamHI, BglII, BspHI, FseI, PmeI, PvuII, SalI, SbfI, XbaI and XhoI sites.

EXAMPLE 3

This example illustrates one possible method for construction of constitutive promoter sequences useful in the vectors disclosed herein.

Genomic DNA from of *Paramecium bursaria Chlorella* virus 1 (PBCV-1) is obtained using routine molecular biology techniques. The template DNA is in a PCR with the forward primer A434: 5'cgcgctcgagcgggtgtgatgtgagaac-caatactttgtagcg 3' (SEQ ID NO: 15), that hybridizes to the 5'UTR of VP54, and the reverse primer A430: 5' gccgctc-gagatcgagttattgatactattacaaaag 3' (SEQ ID NO: 16) that hybdrizes to a434L, a protein >800 bp upstream. The amplified product (SEQ DI NO: 17) includes the constitutive VP54 promoter, plus protein A431L coding sequence.

The resulting 812 bp product is cleaved with XhoI and cloned into the vector pMF124cGFPble (Fuhrmann et al, (1999) A synthetic gene coding for the green fluorescent protein (GFP) is a versatile reporter in *Chlamydomonas reinhardtii*. Plant J. 19:353-361). This cloning step replaces the vector's rbcS2 promoter with the new promoter of interest, and retains the bleomycin and codon-optimized GFP coding sequences, plus the rbcS2 3' untranslated sequence of the pMF124cGFPble. GFP fluorescence or resistance to phleomycin in transformed algae is determined to confirm promoter activity in the transformed alagae. Genes and sequences of interest can be operably linked to the VP54 promoter.

Alternatively, the promoter sequence is cloned into the multicloning site an IGS 'baseline' vector, including but not limited to the baseline vectors described above for *Chlamydomonas* or *Chlorella*, followed by a gene of interest and other appropriate regulatory sequences such as a 3' UTR.

EXAMPLE 4

This example illustrates one possible method for construction of inducible promoter sequences and 3'UTRs, useful in the vectors disclosed herein.

To engineer an insert containing a NIT1 inducible promoter sequence from *Chlamydamonas*, sequence analysis of the probable transcription promoter of NIT1 was performed. Sequence analysis revealed a putative CCAAT box at −836, a TFII-I binding site at −664, a TFII-A binding site at −509, and a CCAAT box at −245, relative to the translational start site. Routine molecular biology techniques are used to amplify and clone the DNA sequence of SEQ ID NO: 1 or a functional fragment thereof into the vectors disclosed herein.

To engineer an insert containing an AMT1 inducible promoter sequence from *Chlamydamonas*, sequence analysis of the probable transcription promoter of AMT1 was performed. Sequence analysis revealed a putative TFII-I binding site at −540 and TFIIA binding site at −192 from the translational start. Routine molecular biology techniques are used to amplify and clone the DNA sequence of SEQ ID NO: 2 or a functional fragment thereof into the vectors disclosed herein.

To engineer an insert containing an AMT2 inducible promoter sequence from *Chlamydomonas*, sequence analysis of the probable transcription promoter of AMT2 was performed. Sequence analysis revealed a putative CCAAT box located at −1020 from the translational start. Routine molecular biology techniques are used to amplify and clone the DNA sequence of SEQ ID NO: 19 or a functional fragment thereof into the vectors disclosed herein.

To engineer an AMT4 inducible promoter sequence from *Chlamydomonas*, sequence analysis of the probable transcription promoter of AMT4 was performed. Sequence analysis revealed a putative TFIIA binding site located at −378 relative to the translational start. Routine molecular biology techniques are used to amplify and clone the DNA sequence of SEQ ID NO: 21 or a functional fragment thereof into the vectors disclosed herein.

To engineer an Rh1 inducible promoter sequence from *Chlamydomonas*, sequence analysis of the probable transcription promoter of Rh1 was performed. Sequence analysis revealed a putative CCAAT box located at −736 relative to the translational start and a putative TFIIA binding site located at −685 relative to the translational start. Routine molecular biology techniques are used to amplify and clone the DNA sequence of SEQ ID NO: 23 or a functional fragment thereof into the vectors disclosed herein.

To generate inserts with 3'UTR sequences that are useful for the regulation of transgene expression in the nuclei of bioprocess algae, routine molecular biology techniques are used to amplify any of the sequences of SEQ ID NO: 18 (the AMT1 3' UTR from *Chlamydomonas*), SEQ ID NO: 20 (the AMT2 3' UTR from *Chlamydomonas*) SEQ ID NO: 22 (the AMT4 3' UTR from *Chlamydomonas*), SEQ ID NO: 24 (the 3' UTR from the Rh1 gene of *Chlamydomonas*), or functional fragments thereof. The amplification products can be cloned into any of the vectors disclosed herein in a location, e.g. operably linked to the 3' end of a gene or sequence of interest. As such the 3' UTRs regulate transcript stability and translation of the gene or sequence of interest.

EXAMPLE 5

This example illustrates one possible method for nuclear transformation.

Nucleic acid uptake by eukaryotic microalgae is by using one of any such methods as electroporation, magnetophoresis, and particle bombardment. This specific example describes a preferred method of transformation by electroporation for *Dunaliella* and *Tetraselmis* using a nuclear expression vector, and can be adapted for other algae, vectors, and selection agents by those skilled in the art. The protocol is not limited to uptake of nucleic acids, as other payload such as quantum dots are also shown to be internalized by the cells following treatment.

Cells of *Dunaliella* are grown in 0.1 M NaCl or 1.0 M NaCl Melis medium, with 0.025 M $NaHCO_3$, 0.2 M Tris/Hcl pH 7.4, 0.1 M $KNO_3$, 0.1 M $MgCl_2.6H_2O$, 0.1 M $MgSO_4.7H_2O$, 6 mM $CaCl2.6 H_2O$, 2 mM $K_2HPO_4$, and 0.04 mM $FeCl_3.6 H_2O$ in 0.4 mM EDTA, to a cell density of $1\text{-}4\times10^6$ cells/mL and adjusted preferably to a density of $1\text{-}3\times10^6$ cells/mL. Cells of *Tetraselmis* spp. are grown in 100% ASW. Approximately 388 uL of the cells per 0.4 cm parallel-plate cuvette are used for each electroporation treatment. Cells, spun down in a 1.5 ml microcentrifuge tube for 4 min at 14,000 rpm or until a pellet forms to enable removal of the supernatant, are resuspended immediately in electroporation buffer consisting of algae culture medium amended with 40 mM sucrose. Transforming plasmid DNA (4-10 ug, preferably the latter), previously linearized by an appropriate enzyme are added along with denatured salmon sperm carrier DNA, (80 ug from 11 mg/mL stock, Sigma-Aldrich), per cuvette. A typical reaction mixture includes 388 uL cells, 4.4 uL DNA, 7.3 uL carrier DNA for a 400 uL total reaction volume. The mixture is transferred to a cuvette for placement on ice for 5 min prior to electroporation. Treatment settings using a BioRad Genepulser Xcell electroporator range from 72, 297, 196 and 396 V at 50 microFaraday, 100 Ohm and 6.9 msec. Negative controls consist of cells in buffer with nucleic acids that receive no electroporation or cells that are electroporated in the absence of payload.

Following electroporation, the contents of each cuvette are plated, with 200 ul of cell suspension plated onto 1.5% agar-solidified medium comprised of 0.1 Melis or 1.0 M Melis medium, as above, in 6-cm plastic Petri dishes, and the remaining 200 uL spread over a selection plate of algae medium amended with 600 ug/mL chloramphenicol. Alternatively, a warmed (38° C.) 0.2% top-agar in algae medium can be used for ease of plating using a 1:1 dilution with cells for 400 uL total per plate. This ensures uniform spreading of the cells on the plate. Plates are dried under low light (<10 umol/m² sec) before wrapping with Parafilm and moved under higher light (50-100 umol/m² sec, preferably 50-60 umol/m² sec). *Dunaliella* may be left in electroporation buffer for 60 hr at room temperature prior to plating with no noticeable affect on cell appearance or motility. In another manifestation, the contents of each cuvette are cultured in liquid medium rather than on solidified medium. Samples treated under the same parameters are collected in well of a 24-well plate, diluted 1:1 with algae growth medium for total volume of 800 uL. These are placed under 50 umol/m² sec for 2 days. Then enough chloramphenicol added for a concentration of 500-800 ug/mL per selection well, and more preferably of 600 ug/mL chloramphenicol for the initial cell density employed.

Algae cells containing inserted nucleic acid payload can be enriched and cultured following flow cytometry. Cells cultured after treatment and sorting by flow cytometry are free of contamination, proliferate, and can be increased in volume as with any other cell culture as is known in the art. Cells can be preserved with paraformaldehyde, to stop motion of flagellated cells, and observed under the light microscope. No significant differences in cell appearance are observed between the electroporated samples and the controls, confirming that electroporation of cells followed by flow cytometry will yield live, non-compromised cells for subsequent plating experiments.

Cells treated by electroporation are examined fluorimetrically two days after treatment for transient expression of reporter gene fluorescence compared to controls receiving no transgenesis treatment. Expression of beta-glucuronidase enzyme in *Dunaliella* follows four different electroporation treatments, using a BioRad GenePulser Xcell electroporator range from 72, 297, 196 and 396 V at 50 microFaraday, 100 Ohm and 6.9 msec, using linearized nuclear expression vector pBI426 with the Cauliflower Mosaic Virus 35S promoter. Expression was measured as absolute fluorescence per microgram protein per microliter sample over time using the 4-MUG assay (R A Jefferson, Assaying chimeric genes in plants: The GUS gene fusion system, Plant Molecular Biology Reporter 5: 387-405; 1987) using the MGT GUS Reporter Activity Detection Kit (Marker Gene Technologies, Eugene Oreg., #M0877) with a Titertek Fluoroskan fluorimeter in 96-well flat-bottomed microtitre plates. There is a detection level of 1 pmol 4-methylumbelliferone up to 6000 pmol per well, with a performance range of excitation wavelength 330-380 nm and emission wavelength 430-530 nm. Fluorescence increased over 90 min for all four electroporation conditions but remained zero for the negative control among four replicate wells for each treatment.

Further, *Dunaliella* and *Tetraselmis* cells are conferred stable resistance to chloramphenicol by electroporation treatment with PmlI-linearized vector pDs69r-CAT-IPPI. Electroporation of cells, at a density of $2\times10^6$ cells/mL in 1 M NaCl Melis medium and pre-chilled for 5 min, is carried out using 396 V at 50 microFaraday, 100 Ohm and 6.9 msec, and cells from each cuvette are plated in a well of a 24-well plate diluted with 400 ul of fresh growth medium. Selection commences on Day 3 using 5 different concentrations of selection agent, namely 0, 500, 600, 700, 800 ug/mL chloramphenicol for a total of 0.8 mL in each well, with two to four replicates of each plating concentration. Cells are cultured under 50-60 umol/m² sec, in a 14 hr day/10 hr night at a temperature range preferably of 23° C. to 28° C. Sensitivity to the antibiotic is seen as a yellowing-bleaching of the cells and change in motility for both *Dunaliella* and *Tetraselmis* when viewed under 400× using an Olympus 1X71 inverted epifluorescent microscope.

At Day 4, about 50% of the cells plated in 600 ug/mL chloramphenicol after electroporation without DNA (negative controls) are green and moving in circles rather than the more common directional swimming. About 20% of the cells plated in 600 ug/mL chloramphenicol after electroporation with DNA are green, with some moving directionally as opposed to spinning in circles. Cells in liquid medium without antibiotic (positive controls) are predominantly green and moving directionally or are settled on the bottom of the plate and immobile. On Day 12, cells not settled on the well bottom are subcultured into new plates with an addition of equal volume of fresh medium±antibiotic per well. Cells that have adhered to the wells are incubated in fresh medium in the existing wells. By Day 13, all negative control cells are bleached and immobile in all levels of antibiotic. Positive control cells are green and motile; those settled on well surfaces remain green but are largely immobile. Cells treated with pDs69r-CAT-IPPI and plated in chloramphenicol show some green cells that are moving both directionally or in circular motion, even in 700 and 800 ug/mL chloramphenicol. By Day 22, all negative control cells remain bleached and immobile; positive control cells remain predominantly green and motile; and a number of cells treated with DNA are identified as being transformed based on being green, motile (documented by video), and in some cases being rounded with the appearance of imminent division. Replicated experiments illustrate that about 8% of the cells plated in 600 ug/mL chloramphenicol after electroporation with DNA are green at Day 10, whereas all controls in 600 ug/mL chloramphenicol are completely bleached. The chloramphenicol-resistant cells retain motility, with slow directional or spinning motion unless settled on the well bottoms. Wells with 700 ug/mL chloramphenicol have fewer green cells, approximated at 3%, and show slow motion in place. Upon transfer to fresh medium, green cells recover directional motion whereas all negative control cells remain bleached and immobile.

Similar results are observed after two weeks when cells are treated with electroporation conditions of 297, 196 or 396 V at 50 microFaraday, 100 Ohm and 6.9 msec, and plated only in 0 or 600 ug/mL chloramphenicol; all replicates of the negative controls in antibiotic are bleached, positive controls are green, and DNA-treated cells have some green, motile algae present. Based on this vector and method, cultures are pooled and enriched for stably transformed cells at Day 12 using flow cytometry with a 680 nm bandpass filter for chlorophyll fluorescence detection, and grown out under diminishing antibiotic concentrations with weekly dilution by 100 uL growth medium lacking chloramphenicol. Alternatively, cultures are supplemented weekly with fresh medium with or without antibiotic for an additional 14-21 days prior to bulking in flask culture. Other selection agents such as gluphosinate can be similarly utilized.

EXAMPLE 6

This example illustrates one possible method of genetic transformation with such vectors as described in the Examples using a converging magnetic field for moving pole magnetophoresis. The magnetophoresis reaction mixture is prepared beginning with linear magnetizeable particles of 100 nm tips, tapered or serpentine in configuration, with any combination of lengths such as, but not limited to 10, 25, 50, 100, or 500 um, comprised of a nickel-cobalt core and optional glass-coated surface, suspended in approximately 100 uL of growth medium in 1.5 mL microcentrifuge tubes, the volume being adjusted downward to account for any extra volume needed if using dilute vector DNA stock. To this is added 500 uL algae cells, such as *Dunaliella* cells, concentrated by centrifugation to reach a cell density of $2$-$4 \times 10^{\wedge}8$ cells/mL in algae medium such as 0.1 M or 1.0 M NaCl Melis medium as determined by hemacytometer counting; the algae cell volume is adjusted as necessary to meet the total volume. Denatured salmon sperm carrier DNA (7.5 uL from 11 mg/mL stock, Sigma-Aldrich; previously boiled for 5 min), and linearized transforming vector (8 to 20 ug from a 1 mg/mL preparation) are added next. Finally 75 uL of 42% polyethylene glycol (PEG) are added immediately before treatment and mixed by inversion. The filter-sterilized PEG stock consists of 21 g of 8000 MW PEG dissolved in 50 mL water to yield a 42% solution. Total reaction volume is 690 uL.

For moving pole magnetophoresis for microalgae treatment, the microcentrifuge tube containing the reaction mixture is positioned centrally and in direct contact on a Corning Stirrer/Hot Plate set at full stir speed (setting 10) and heat at between 39° to 42° C. (setting between 2 and 3), preferably at 42° C. A 2-inch×¼-inch neodymium cylindrical magnet, suspended above the reaction mixture by a clamp stand, maintains dispersal of the nanomagnets. After 2.5 min of treatment the mixture is transferred to a sterile container that holds at least 6-10 mL, such as a 15 mL centrifuge tube. A dilution is made by adding 1.82 mL of algae culture medium to the mixture, to allow a preferred plating density. To this is added 2.5 ml of dissolved top-agar (autoclaved 0.2% agar in algae medium such as 0.1 M NaCl Melis) at 38° C. (1:1 dilution). Mix and plate 500 uL of solution per 6-cm plate containing algae medium such as 0.1 M NaCl Melis medium prepared with and without selection agent for selection of transformants under cell survival densities. Allow plates to dry for 2-3 days under low light ($<10$ umol/m$^2$ sec). When dry, plates are wrapped in Parafilm and cultured under higher light of 85-100 umol/m$^2$-sec. Plates are observed for colony growth beginning at day 10 and ending no later than day 21, depending on the antibiotic, after which colonies are photographed and subcultured to fresh selection medium.

Typical data are exemplified by dark green colonies of *Dunaliella* salina formed on medium containing 0.5 M phleomycin in replicated plates 3 weeks after magnetophoresis treatment of 2.5 min with linearized *Chlamydomonas* nuclear expression vector pMFgfpble using 25-micron tapered nanomagnets. Controls treated in the absence of DNA are unable to grow on 0.5 M phleomycin but form multiple colonies on 0.1 M Melis medium lacking antibiotic. Further typical data are exemplified by small dark green colonies of *Dunaliella* salina formed on medium containing 100 ug/mL chloramphenicol 12 days after magnetophoresis treatment with linearized *Dunaliella* expression vector pDs69r-CAT-IPPI. This level of antibiotic gives 100% kill of cells after treatment by magnetophoresis in the absence of transforming DNA, as the final plating density of remaining viable cells is lower than the initial treatment density of viable cells. At Day 12 these colonies are subcultured to a fresh plate of medium containing 100 ug/mL chloramphenicol. By Day 23 the resistant colonies continue to grow while all negative controls on replicated selection plates are already non-viable by Day 12. Using this general strategy, additional *Dunaliella* and *Tetraselmis* transformants may be generated.

EXAMPLE 7

This example describes one possible method of introduction of nucleic acids into target algae by particle inflow gun bombardment. These conditions introduce nucleic acids representative of oligonucleotides into target algae, including but not limited to plasmid DNA sequences intended for transformation. Microparticle bombardment employs a Particle Inflow Gun (PIG) fabricated by Kiwi Scientific (Levin, New Zealand).

Cells in log phase culture are counted using a hemacytometer, centrifuged for 5-10 min at 1000 rpm, and resuspended in fresh liquid medium for a cell density of $1.7 \times 10^{\wedge}8$ cells/ml. From this suspension 0.6 ml will be applied to each 10-cm plate solidified with 1.2% Bacto Agar. To allow cells a recovery period before antibiotic selection is applied, some plates use nylon filters overlaid on the agar; for direct selection no filters are used. Plates placed 10 cm from the opening of the Swinnex filter (SX0001300, Millipore, Bedford Mass.) are treated at 70 psi with a helium blast of 20 milliseconds with the chamber vacuum gauge reading −12.5 psi at the time of blast. These PIG parameters were optimized for depth penetration and lateral particle distributions using dark field microscope and automated image processing analyses courtesy of Seashell Technologies (La Jolla, Calif.). Preferred conditions result in 60-70% of the particles penetrating to a depth of between 6-20 microns. Transforming DNA is precipitated onto S550d DNAdel™ (550 nm diameter) gold carrier particles using the protocol recommended by the manufacturer (Seashell Technology, La Jolla, Calif.), with 60 ug particles and 0.24 ug DNA delivered per shot. Three shots are made per plate, targeted to different regions of cells. After shooting, plates are sealed with Parafilm and placed at ambient low light of 10 uM/m²-sec or less for two days. On Day 3, the cells on nylon filters are transferred to Petri dishes or rinsed and cultured in liquid medium in multiwell plates with any desired selection medium. Using this general strategy, additional *Chlorella, Chlamydomonas, Dunaliella* and *Tetraselmis* transformants may be generated.

In an additional exemplified embodiment, *Chlorella, Dunaliella, Chlamydomonas* and *Tetraselmis* can be transformed using the Bio-Rad Biolistic PDS-1000/He Particle Delivery System (Bio-Rad Laboratories, Hercules, Calif.). Rupture disks of varying strengths may used (1100, 1350, and 1500 psi), preferably 1350 psi. Tungsten, M17 (1.1 μm median diameter) or more preferably, gold particles (0.6 or 0.2 μm median diameter) may be coated with 2-5 μg of plasmid DNA in 5 μl of deionized water to which is added 50 μl of 2.5 M $CaCl_2$ and 50 μl 0.1 M spermidine. Approximately $5 \times 10^7 - 10^8$ *Chlorella* or *Tetraselmis* cells are spread on artificial seawater (ASW) or F agar medium, or $5 \times 10^7 - 10^8$ *Chlamydmonas* cells are spread on Tris-Acetate-Phosphate (TAP) agar medium, or $5 \times 10^7 - 10^8$ *Dunaliella* cells are spread on 1 M Melis agar medium and air dried before bombardment. Bombarded cells are allowed to recover overnight on agar medium with ambient illumination of 20 μE/m2/sec or less. On the following day, cells are resuspended in the corresponding liquid medium and incubated for 24 hrs under 12 hours illumination of 20 μE/m2/sec or less for recovery. On the second day after particle bombardment, approximately $10^6$ of these *Tetraselmis* or *Chlorella* cells are plated on ASW or F agar plates supplemented with the appropriate antibiotic; approximately $10^6$ of these *Dunaliella* cells are plated on 1 M Melis agar plates supplemented with the appropriate antibiotic; approximately $10^6$ of these *Chlamydmonas* cells are plated on TAP agar plates supplemented with the appropriate antibiotic. Representative selection agents for *Chlamydomonas* are 100 μg/ml spectinomycin or 25 to 50 μg/ml streptomycin, or 50 to 100 μg/ml kanamycin or 50 to 100 μg/ml geneticin (G418). Representative selection agents for *Chlorella* are 50 to 100 μg/ml hygromycin or 25 to 50 μg/ml phleomycin, or 50 to 100 μg/ml kanamycin or 25 to 50 μg/ml geneticin (G418). Representative selection agents for *Tetraselmis* are 80 to 100 μg/ml chloramphenicol or 15 to 20 μg/ml gluphosinate. Representative selection agents for *Dunaliella* are 0.5 M phleomycin or 600 μg/ml chloramphenicol or 14 to 16 μg/ml gluphosinate. Plates are placed under constant illumination for 2 weeks and transformed colonies appear as larger dark green colonies against a background of pale green small colonies.

EXAMPLE 8

In an exemplified embodiment of this invention, one or more algal lines are identified as showing a statistical difference in fluorescence, isoprenoid flux, or fatty acid content compared to the wild-type; identification of any line showing no statistical difference despite transgene expression of IPPI or accD under various promoters is also a measurable embodiment. *Chlamydmonas, Chlorella, Dunaliella* and *Tetraselmis* are ideal candidates for characterization and selection by flow cytometry and by High Pressure Liquid Chromatography (HPLC) due to the non-aggregating nature of cultures and their pigmentation, respectively. Flow cytometry is used to select for cells with altered isoprenoid flux, or other measurable altered fluorescence or growth characteristics, resulting from payload uptake, nucleic acid integration, or transgene expression. Cultures can be preserved with 0.5% paraformaldehyde, then frozen to −20° C. Thawed samples are analyzed on a Beckman-Coulter Altra flow cytometer equipped with a Harvard Apparatus syringe pump for quantitative sample delivery. Cells are excited using a water-cooled 488 nm argon ion laser. Populations were distinguished based on their light scatter (forward and 90 degree side) as described in previous Examples. Resulting files are analyzed using FlowJo (Tree Star, Inc.). Cell lines of interest are then bulked up for further characterization, such as for pigments, nucleic acid content or fatty acid content.

HPLC is used for analysis of IPPI lines, to assess pigmented isoprenoids likely affected by the expression of this rate-limiting enzyme. Cells are filtered through Whatman GF/F filters (2.5 cm), hand-ground, and extracted for 24 hr (0° C.) in acetone. Pigment analyses are performed in triplicate using a ThermoSeparation UV2000 detector ($\lambda$=436 nm). Eluting pigments are identified by comparison of retention times with those of pure standards and algal extracts of known pigment composition. The numbers reported are pigment concentrations in ng/L; data are then converted to amount per million cells, based on total cell number in each sample. Means analysis by Student's t test is done to reveal any significant increase in intermediate and endpoint carotenoids relative to chlorophyll a, and indicate possible functionality of the inserted genes for increasing isoprenoid flux. Cell lines of interest are bulked up for further characterization by transgene detection and by fatty acid content. For the latter, nucleic acids are prepared any number of standard protocols. Briefly, cells are centrifuged at 1000×g for 10 min. To the cell pellet, 500 uL of lysis buffer (20 mM Tris-HCl, 200 mM Na-EDTA, 15 mM NaCl, 1% SDS)+3 uL of RNAase are added and incubated at 65° C. for 20 min. This was mixed intermittently. After centrifugation at 10,000×g for 5 min the supernatant is transferred to a new centrifuge tube. Extraction of DNA is done by adding equal volumes of phenol-chloroform-isoamyl alcohol (24:24:1), followed by centrifugation. The aqueous layer is then transferred to a new 1.5 mL Eppendorf tube, and the DNA is precipitated with 2 vol of 100% ethanol. After precipitation, the DNA pellet is washed with 70% ethanol, and dissolved in TE buffer (10 mM Tris-HCl, 1 mM EDTA, pH 8.0). The concentration of the DNA is ascertained spectrophotometrically. Primers are designed for within inserted genes and within chloroplast sequences as is known in the art, and PCR conditions for each primer set is determined using standard practices. Amplified DNA can be sequenced to verify presence of target nucleic acids.

Lipid content and composition is assessed by fatty acid methyl-ester (FAME) analysis, using any number of protocols as is known in the art. In one exemplification, cell pellets are stored under liquid nitrogen prior to analysis. Lipids are extracted using a Dionex Accelerated Solvent Extractor (ASE; Dionex, Salt Lake City) system. The lipid fraction is evaporated and the residue is heated at 90° C. for 2 hr with 1 mL of 5% (w/w) HCl-methanol to obtain fatty acid methyl esters in the presence of C19:0 as an internal standard. The methanol solution is extracted twice with 2 mL n-hexane. Gas chromatography is performed with a HP 6890 GC/MS equipped with a DB5 fused-silica capillary column (0.32 µm internal diameter×60 m, J&W Co.). The following oven temperature program provides a baseline separation of a diverse suite of fatty acid methyl esters: 50° C. (1 min hold); 50-180° C. (20° C./min); 180-280° C. (2° C./min); 280-320° C. (10° C./min); and 320° C. (10 min hold). Fatty acid methyl esters are identified on the basis of retention times, co-injection analysis using authentic standards, and MS analysis of eluting peaks.

In another exemplification, lipid content is measured by extraction of trans-esterified or non-trans-esterified oil from *Tetraselmis* and *Dunaliella* (E. Molina Grima, A. Robles Medina, A. Gimenez Gimenez, J. A. Sanchez Peres, F. Garcia Camacho and J. L. Garcia Sanchez. Comparison between extraction of lipids and fatty acids from microalgal biomass. J. American Oil Chemists' Society: 71 (9): 595-599; 1994; E. G. Bligh, W. J. Dyer. A rapid method for total lipid extraction and purification. Can. J. Biochem. Physiol. 37:911-917; 1959). To begin, 60 L of algal cells are harvested using a concentrator to reduce the liquid to 3 L. The volume can be further reduced by centrifugation at 5000 rpm for 15-30 min, forming a 1200 mL pellet. The cell pellet is lyophilized for 2 days, yielding the following weights: *Dunaliella* spp −14.21 g dry weight, 45 g wet weight; *Tetraselmis* spp. −48.45 g dry weight, 50 g wet weight. These were stored at −20° C. in 50 mL tubes. For extraction, lyophilized biomass weighing 15.39 g for *Tetraselmis* and 14.2 g for *Dunaliella* are employed. To the lyophilized biomass, 1140 mL of the corresponding extraction system in a conical flask is carried on for 1 h in nitrogen atmosphere with constant agitation (300:600:240 ml of $Cl_3CH/MeOH/H_2O$, 1:2:0.8, vol/vol/vol, monophasic). The mixture is then filtered through glass filters (100-160 µm bore). The residue is washed with 570 mL of the extraction system, and this filtrate is added to the first one. The mixture is made biphasic by the addition of 450 mL chloroform and 450 mL water, giving an upper hydromethanolic layer and a lower layer of chloroform in which lipids are present. This is shaken well and left for an hour to form a clear biphasic layer. The lower chloroform layer that has the lipids is collected and excess chloroform is evaporated using a rotary evaporator for 2 hr until droplets of chloroform form. The remaining lipids in the hydrophilic phases, as well as other lipids, are extracted with 100 mL chloroform. The total volume is reduced to 10 mL in a vacuum evaporator at 30° C. The extract is further subjected to a speed vacuum overnight to remove excess water and chloroform. For *Tetraselmis* spp. CCMP908, for example, 2.735 g oil was obtained from 48.45 g dry weight for an approximate 18% oil content for the cells. For *Dunaliella* spp, 4.4154 g oil was obtained from 14.21 g dry weight for an approximate 31% oil content for cells, without accounting for salt residues that can be removed by 0.5 M ammonium bicarbonate. The methodology can be scaled down, for example to allow analyses with mg quantities.

EXAMPLE 9

In an exemplified embodiment of this invention, one or more algal lines identified to be of interest for scale-up and large-scale culture are taken from flask culture into carboys then into outdoor photobioreactors. Ponds or raceways are an additional option, as are covered photobioreactors. All field production is subject to appropriate permitting as necessary. Lab scale-up can occur, as one example, from culture plates to flask volumes of 25 mL, 125 mL, 500 mL, then into indoor or outdoor carboy other vessel volumes of 2.5 L, 12.5 L, 62.5 L prior to seeding of bioreactors such as the Varicon Aquaflow BioFence System (Worcestershire, Great Britain) at 200 L, 400 L, 600 L and 2400 L volumes. Other options can be systems from IGV/B. Braun Biotech Inc. (Allentown Pa.) and BioKing BV ('s-Gravenpolder, The Netherlands) or vertical tubular reactors of approximately 400 L volumes employed commercially such as at Cyanotech Corp. (Kona Hi.). Culture can proceed under increasing light conditions so as to harden-off the algae for outdoor light conditions. This can be from 100, 200, 400, 600 $uE/m^2$-sec indoors to 1200 to 2000 $uE/m^2$-sec outdoors. Culture of algae in photobioreactors, degassing, pH monitoring, dewatering for biomass harvest, and oil extraction proceeds as described (Christi, Y. Biodiesel from microalgae. Biotechnology Advances 25: 294-306; 2007). Photobioreactors have higher density cultures and thus can be combined for biphasic production with a raceway pond as the final 1-to 2-day grow-out phase under oil induction conditions such as nitrogen stress. This includes varying levels of ammonium and/or nitrate. Alternatively, production of biomass for biofuels using raceways can proceed as is known in the art (Sheehan J, Dunahay T, Benemann J, Roessler P. A look back at the US Department of Energy's Aquatic Species Program-biodiesel from algae. National Renewable Energy Laboratory, Golden Colo., Report NREL/TP-580-24190: 145-204; 1998). Numerous systems are suitable for addition of carbon dioxide from sources such as flue gas from biorefineries or power plants under various levels of culture pH, carbonate/bicarbonate salts, or other means of retaining the soluability of $CO_2$ within the culture media.

While the present teachings have been described in terms of these exemplary embodiments, the skilled artisan will readily understand that numerous variations and modifications of these exemplary embodiments are possible without undue experimentation. All such variations and modifications are within the scope of the current teachings.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein.

In this application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. Additionally, in this application, "and/or" denotes that both the inclusive meaning of "and" and, alternatively, the exclusive meaning of "or" applies to the list. Thus, the listing should be read to include all possible combinations of the items of the list and to also include each item, exclusively, from the other items. The addition of this term is not meant to denote any particular meaning to the use of the terms "and" or "or" alone. The meaning of such terms will be evident to one of skill in the art upon reading the particular disclosure.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A vector for the nuclear integration and expression of one or more genes of interest or sequences complementary to said one or more genes of interest in unicellular bioprocess algae, said vector comprising:
   - an algal-specific nuclear promoter or an algae virus promoter operably linked to said gene of interest or sequence complementary to said gene of interest; and
   - an intergenic spacer region (IGS) of an rRNA locus, said IGS comprising a terminator, an enhancer, a spacer promoter, a proximal terminator, an upstream promoter element, and a promoter core comprising an rInr.

2. The vector of claim 1 wherein said algal-specific nuclear promoter is selected from the group consisting of: an algal-specific ammonium transporter (AMT1) promoter, an algal-specific ammonium transporter (AMT2) promoter, an algal-specific ammonium transporter (AMT4) promoter, an algal-specific nitrate reductase (NIT1) promoter, and an algal-specific Rhesus (RH1) promoter.

3. The vector of claim 1 wherein said algal virus promoter is a *Paramecium bursaris Chlorella* virus 1 VP54 promoter.

4. The vector of claim 1, wherein said unicellular bioprocess algae is selected from the group consisting of *Dunaliella, Tetraselmis, Chlorella* and *Chlamydomonas*.

5. The vector of claim 1, wherein the IGS flanks and is operably linked to 5' end of the algal-specific nuclear promoter and the 3' end of the gene of interest or sequence complementary to said gene of interest.

6. The vector of claim 1 wherein said algal-specific nuclear promoter is a promoter specific to an algal species selected from the group consisting of *Dunaliella, Tetraselmis, Chlorella* and *Chlamydomonas*.

7. The vector of claim 1, wherein said vector comprises a gene of interest, and wherein said gene of interest encodes a molecule selected from the group consisting of IPP isomerase, acetyl-coA synthetase, pyruvate dehydrogenase, pyruvate decarboxylase, acetaldehyde dehydrogenase, α-carboxyltransferase, β-carboxyltransferase, biotin carboxylase, biotin carboxyl carrier protein, acyl-ACP thioesterase, 3-ketoacyl-ACP synthetases I, II and III, ATP citrate lyase, carbonic anhydrase, fatty acid desaturases, Rh1 $CO_2$ transporters, and acyl-CoA diacylglycerol acyltransferase.

8. The vector of claim 1, wherein said vector comprises a sequence complementary to a gene of interest, and wherein said sequence facilitates antisense, hairpin, or siRNA transcripts.

9. The vector of claim 1, wherein said IGS comprises a series of terminators, enhancers, the spacer promoter, the proximal terminator, the upstream promoter element, and the promoter core comprising the rInr.

10. A unicellular bioprocess alga for gene expression comprising:
    - a unicellular bioprocess algae transformed with a vector for the nuclear integration and expression of one or more genes or sequences complementary to one or more genes of interest, said vector comprising:
    - an algal-specific nuclear promoter or an algal virus promoter;
    - a gene of interest or sequence complementary to a gene;
    - an algal-specific terminator; and
    - an intergenic spacer region of an rRNA locus, said intergenic spacer region comprising a terminator, an enhancer, a spacer promoter, a proximal terminator, an upstream promoter element, and a promoter core comprising an rInr,
    - wherein said gene of interest or said sequence complementary to said gene is operably linked to said algal-specific promoter.

11. The unicellular bioprocess alga for gene expression of claim 10, wherein said bioprocess alga is selected from the group consisting of *Dunaliella, Tetraselmis, Chlorella* or *Chlamydomonas*.

12. The unicellular bioprocess alga for gene expression of claim 10, wherein said algal-specific nuclear promoter is selected from the group consisting of: an algal-specific ammonium transporter (AMT1) promoter, an algal-specific ammonium transporter (AMT2) promoter, an algal-specific ammonium transporter (AMT4) promoter, an algal-specific nitrate reductase (NIT1) promoter, and an algal-specific Rhesus (RH1) promoter.

13. The unicellular bioprocess alga for gene expression of claim 10, wherein said algal virus promoter is the *Paramecium bursaris Chlorella* virus 1 VP54 promoter.

14. The unicellular bioprocess alga of claim 10, wherein said intergenic spacer region comprises a series of terminators, enhancers, the spacer promoter, the proximal terminator, the upstream promoter element, and the promoter core comprising the rInr.

15. A method for producing a gene product of interest in an alga comprising transforming an alga with a vector according to claim 1.

16. The method of claim 15, wherein an alga nucleus is transformed.

17. The method of claim 15, further comprising:
    - culturing said alga, thereby producing the product of interest; and
    - collecting the gene product of interest from the cultured algae.

18. The method of claim 15, wherein said algal-specific nuclear promoter is selected from the group consisting of: an algal-specific AMT1 promoter, an algal-specific AMT2 promoter, an algal-specific AMT4 promoter, an algal-specific nitrate reductase (NIT1) promoter, and an algal-specific RH1 promoter.

19. The method of claim 15, wherein said algal virus promoter is the *Paramecium bursaris Chlorella* virus 1 VP54 promoter.

20. The method of claim 15, wherein said alga is selected from the group consisting of *Dunaliella, Tetraselmis, Chlorella* and *Chlamydomonas*.

21. A method of making a unicellular bioprocess alga for gene expression comprising transforming a unicellular bioprocess alga with a vector according to claim 1.

22. The method of claim 21, wherein said transforming is carried out using magnetophoresis, electroporation, or a particle inflow gun.

23. The method of claim 21, wherein said one or more genes of interest or one or more sequences complementary to one or more genes of interest is introduced into the nucleus.

24. The method of claim 21, wherein said one or more genes of interest encodes a selectable marker.

25. The method of claim 21, wherein said vector comprises a gene of interest that encodes a molecule selected from the group consisting of IPP isomerase, acetyl-coA synthetase, pyruvate dehydrogenase, pyruvate decarboxylase, acetaldehyde dehydrogenase, α-carboxyltransferase, β-carboxyltransferase, biotin carboxylase, biotin carboxyl carrier protein, acyl-ACP thioesterase, 3-ketoacyl-ACP synthetases I, II and III, ATP citrate lyase, carbonic anhydrase, fatty acid desaturases, RH1 $CO_2$ transporters and acyl-CoA diacylglycerol acyltransferase.

26. The method of claim 21, wherein said vector comprises a sequence complementary to said gene of interest that facilitates antisense, hairpin, or siRNA transcripts.

27. The vector of claim 1, wherein said vector comprises a first algal-specific nuclear promoter or algal virus promoter and a second algal-specific nuclear promoter or algal virus promoter, and wherein said first and second algal-specific nuclear or algal virus promoters are operably linked to a first gene of interest and a second gene of interest, respectively.

* * * * *

SEQUENCE LISTING

```
<160> NUMBER OF SEQ ID NOS: 26

<210> SEQ ID NO 1
<211> LENGTH: 1003
<212> TYPE: DNA
<213> ORGANISM: Chlamydamonas reinhardtii

<400> SEQUENCE: 1
ggcgtgggct ctgtatggct gggtaacggt acgtataatt ccaggtacaa gctagagcag     60
acggtggtga gaagcattag aagcattgtc ccgagtgtgg tggctagaat cccggcccac    120
gaatcacagt gaatgggtac atgtacaggt gccccgccag ccccgctcc tctgctgcct    180 ctgatgcctc atgccaaaag tcctgacgcg gcgccctcac atccccgtcc gggtaatcta    240
tgagtttccc ttatcgagca tgtacgcgat agtggacggg gctcagggtg gggggtgggt    300
gggtgggagg ggcgttcctt cagacaccct ggaggggtgg ctagaaaagc ggccgcgcgc    360
cagaaatgtc tcgctgccct gtgcaataag caccggctat attgctcagc gctgttcggc    420
gcaacggggg gtcagccctt gggaagcgtt ggactatatg gtagggtgcg agtgaccccg    480
cgcgacttgg agctcgatgg ccccgggttg tttggggcgt ccgcctctcg cgctattctg    540
agctggagac cgaggcgcat gaaaatgcat tcgcttccat aggacgctgc attgtggctt    600
gaaggttcaa gggaagggtt caaacgaccc cgccgtacga acttttgtcg gggggcgctc    660
ccggccccgg gctcttgtgc gcgcattagg gcttcgggtc gcaagcaaga cgatacagga    720
accgaccaat cgatagtctt gtgcgaccgt gcacgtgtgc agcaatagtt aggtcgataa    780
ccacgttgaa cttgcgtctc tcttcgtggc gcctcctgct tggtgctcca cttcacttgt    840
cgctatatag cacagcgttg aaagcaaagg ccacactaat acagccgggc tcgagagtcc    900
gtctgcgttt gcattgttgg ccaagggctg ctttgtagcc aaagccatac acgaagcttc    960
acttgattag cttacgacc ctcagccgaa tcctgccagt atg                      1003

<210> SEQ ID NO 2
<211> LENGTH: 1034
<212> TYPE: DNA
<213> ORGANISM: Chlamydamonas reinhardtii

<400> SEQUENCE: 2
caggcggcgt tgctgcgctt cgtgacttcc tgcagccgcc cgcctctggg cggtttcaga     60
tacctgcaac cgccgctgac gctgcacaag gtgtgtgtgg gtaaacgggg cagtgcgagg    120
ggcgggtttg gcttgactgt ctttatgtct tgcgtatggc ccgtggccca taaggcacat    180
tggtgaagat ggtgcacatc ctgcttgccg gcagctgcgt tgtgtgcaaa gcccttccaa    240
ccctcgcgcc tttgcctcgt tgccgtcttt ccatccacct gctcctgttc cacgcgtcct    300
atccttaccc cacaggtgga ctgcgacgcg ggcttgttcg cggccatcgg cggtcgtgac    360
gtggaccgcc tgccctccgc ctctacctgc tacaacatgc tcaaactgcc gaactaccgc    420
cgcgccgcca ccctcaaggc taagctgctg tactccatta cctcgggcgc gggctttgag    480
```

```
ctgtcgtaga gagaaggagg ggcggcggga gctgagtaga ggcggggagt agcaggggtc      540
gtaggggaga gcgtgagggc ggccgaggtt cgggccttgg ccgctggcgc gcgcgcgggt      600
cgcgtaaagg cgaggcgagt tgttctttaa agggtaggca ttgataatgt catcggtttg      660
cttcatggtc gtagacgtcg tgtaggaggt gtgtgaagaa gtggagtcga aggtggtcgg      720
gctgaccaga accctagttg gagttaggac tgccctggct gggttgtcat gcgagtcaat      780
ttcactgctg gagaacggcc caccccaagc aagtcggttc atgagttccg tggataggtt      840
gtgtaaggta cgcgaccagt ggacgcgtcg acatgaggga gaaacaaagg gcaacaaagg      900
gtaacgcatc ttggtccgac tccatgcgcc gtggctccat gcagtgtcaa aaccctaacc      960
ttccattctt ttccgacgca ggccttttgt taagccgatc agctctgacc taagttaaaa     1020
tagacacaaa catg                                                      1034

<210> SEQ ID NO 3
<211> LENGTH: 50
<212> TYPE: DNA
<213> ORGANISM: Chlamydomonas reinhardtii

<400> SEQUENCE: 3
acgcgtccta tccttacccc acaggtggac tgcgacgcgg gcttgttcgc                  50

<210> SEQ ID NO 4
<211> LENGTH: 32
<212> TYPE: DNA
<213> ORGANISM: Chlamydomonas reinhardtii
<220> FEATURE:
<221> NAME/KEY: misc_signal
<222> LOCATION: (30)...(32)
<223> OTHER INFORMATION: translation start codon

<400> SEQUENCE: 4
ctctgaccta agttaaaata gacacaaaca tg                                     32

<210> SEQ ID NO 5
<211> LENGTH: 7938
<212> TYPE: DNA
<213> ORGANISM: Chlamydomonas reinhardtii
<220> FEATURE:
<221> NAME/KEY: terminator
<222> LOCATION: (7503)...(7505)

<400> SEQUENCE: 5
tggcagcgcc tgtcctgcgg cgcccattgc cgtttcgggc gtgccgccg ccgtcgccca        60 ccacagcctc actgtatccg gccagcaggg cgcagcccac ggggcagccg ctgccagcga      120
gatcgttgcg tcggtgccct tcctcgcctt ccaacagcag caacagcaaa tggcggcggc      180
ggccgcggcg gctcaccagt atccgcagcc gttcatgagc actgctgtgc tgatgggcgg      240
cgcggccgga ggcggcggtg ccaataacga caggcctttg tttagtgatg acgtaatcgg      300
aatggagacg gcgcttgcac ccgtgcaacc catgcagcag cccgcctaca gccaggcatc      360
cgctgggcct aacaatgtgt agatagggc gggttacagc ccgaaggtgg ggtgcggtgt      420
tgcacgtacg gcgcggcaat gtgcggcgcg cgcggcgatg tatggcgcgc agtttggact      480
gggacagttc ggatgtatga cgtacttcaa taagccaaag acggtcatga tctctttcag      540
gaatggtgtg ttcgaccccc tgttatgttc atactatggg actgcatgtc ctgcgattta      600
tagcaattca agtttggcct cgtctttcag caccggctgc tgaagcgggg gacaaagcat      660
acttcttgct tgtttgcggc tgtttgtagc gggcagtagt gtgaagcaat gagtgggtgc      720
```

```
tagtacgaaa gacttctaac acggaagact tctggtacta gggtaggatt gtggcagtgg      780
cggactggag ttgccagcgc gcctcacgca ctgtttcaca ggtgtgcagt gcccatgtag      840
ctttaaagca cccccgcatc agcagagtat gtgaggagct tgggacattg gtgaatctta     900
ttagcctgcg aggggcgtcg ttcggtgcgt gcttgcgcta gatagtataa cttgtgaatt     960
ctttatgcgt gtagtttgct tttgcaaggc tggttggcaa tctgcgcgag catacgccg     1020 gggcacattc atacgttcta atggtgtaca gtacggtatg cacggccgta acggattgcc     1080
gcacgtgcag ggctagtgac gacggaggtg tggtagggtt agccggcggt gagggaaggc     1140
cggaagccga aagggacgag gcgggccgcg caggagctct gcctccaggc tcacaaggta     1200
cttggggtgc gtgccaaccc ttctggcctc tgctgttgcc cactggtagg tgtcgcctaa     1260
aaccggacgg cattgcgggt ctgttcacct gaggagggtg gttgcataac gcccccgtg     1320 gcgtcatgcg ggcccacaag ctctgccgat ggcaagtact cccacattcc cacttttgaa     1380
gaaatggtga cgggccggca ggccatagca ttgtaggggc ctggtgtgat agcatacagg     1440
tatgtgcgtg tgccgcccgg cgcgcgcatg caacagctca tcctgcactg gggcgggctc     1500
acttcattct acttgagagc ccgcccatca taccgtaatc cagcagttac attctgctct     1560
gtgccggcgg cacaatggcg aacgaccccg gggatgtttg cgcgctcgct gcgcccggtg     1620
tgtgagagct gaggcggacc ggcgagccag ggacgcagtg ccaacgcacc gctgtggaac     1680
ttctctgcgc gcgacccggg tgcgccacga gggggtgcca caattgtaag acacaacgtc     1740
acaaccgccc aggcccctcg cacatgcctc gacccgcacc ctcatggacg atgtcctggc     1800
ctgagaacag gagcgaatac acgactttag ccaatgcttc aggtgtgcct gcgggcctgg     1860
ccgtcgcggc tcgaggtgtg gaaggaaggg cttcgaccat gcgcgtcgcc acgacagagc     1920
tcctcctcta tttgctggac ctcccctaca gacaccatac gcgtgtaact tgctggggcg     1980
ccgagaagca agcgtaagcc ctcgcgtcag tcggggaagg agcacaaggt gtggcacatg     2040
gatagcgtgt cgacctcggc tgggtgcgtc gaaatcgtca tgagtggtat ctgcttaaat     2100
gcctcgacta ccgcttttcca cagactcaag cgctgtcgtt ttctctgaag ttctcccact     2160
gacggtctcg ttagcgtaac tcccctcggc gttgccgaaa tgccctcatg ctttgcatgg     2220
ttcaatacta tgtttatta catgactact ggcatcggaa caactttgga aggaggcccc     2280
agggcaaatc gagaagtttg gttacgcaga agctcgctag caagtcccgc ctctgcgggc     2340
gccattcaca caacttacta tgaacgcctc tgctctccat aatgcgtttg agaacctctc     2400
gacacggggg cctcccccca caccctgtc acaccagccc cacaccgggc gccgtactaa     2460
cgcacatgac ggaatgggcc tcctccttt cctcgtgggc ttaaattcag tcgggcgaga     2520
gatttggtaa ccttgatttc gcggaactca ggccggcaac catgcaggca cttcctccca     2580
agattcccgc ttccgtatcg ggccacggaa cccagtcccg gcgtcacagc ctggactggt     2640
cgcatattgg ccttccctct cgcgagacgc agctgcgggc tggctttgtg tgagtcgtag     2700
ggcgagcgcg gtgcctgtgc gcgcctgtct aaccgcttcg tgccagtggc cgccgcgcgc     2760 gcccctaga aatgcgtccg atgcaagtcc ggcggccgcg ctcggcgcag gccttgctga     2820
tctcacctgt ttcattggct catgtgtgtg gcatttcagg ccctcggctg ctgtggtgat     2880
tgtgattttc gtcggtaagc aagaagccga gcgactacca accttgcgcg cgcgcgttcg     2940
atagtaccgg ccgctttagc gtggcgcctg tttccgcaac cctcatgagc cgaacacatt     3000
cattgcttat agctcttgtg ccgcttccgc cctggggata ggtccaggtc cttccagcat     3060
```

```
gccgcaagcc caacctgcac ttttcccttc cgtcgcaggc ctgttttcg  gcttgaccca   3120 gtacaccgag ttgggcacaa atgcgcagga ggaggtcgat cgcttttaca aatgtaagcg   3180
ctaggtcggc cgctcgtttg aaaatgcagg gtagggctcg cgcgagttcc gcatggtccc   3240 ccccctaca  cacactatcg cgcttctccc cttcctgcaa catgccgctg tcattgccct   3300
ctgcccaaca gacctggtcg atgtcaacat catggtgtgg atcggtttcg gcttcctgat   3360
gaccttcatg cgccgctacg gctacggcgc tgtggccctg aactactttg cctcggcgct   3420
catgttcctg gaggccatcc tcatgatcgg cgccacgcag gtgcgcgtga caaagagagg   3480
gacataaggg tccgcatact gcaagtttgt aatgggcgcg cacggcgcac ctggccgtgc   3540
aaacaacatc gaaagactgg tgaagatctg ctgctccatc caatttcgtg ccttcatccc   3600
agcggccccg ttccttcctg tcctcccaca gcaagtgttc tggaactacc atcgcaccaa   3660
gatccagatc gacatcgcct tgctgatcga ctgcgccttc tgcgccggtg agccgcatgc   3720
gcttgggctg ttacttgccg agatgcatgc cagctaggta cagtaattca gtgcgtaaca   3780
agtcacgggc ttgtgccatt cccatccctg ttctatgttc acgccgtttc ggactcccac   3840
gtcgcattgt accatgctct ggtcccctt  cctgtgcggc gtcgcttgac gtggctcaat   3900
gctacccgtg tgtctccccc gcagcctctg gtatgattgc cttcggcgcc atcatcggca   3960
aggccacgcc cacgcagttg ctgtggctgc tcttttggca ggtgcatgcg tgtcagctga   4020
ttcccgatcg ctagttttag aagctgcgtg ccgcatgaca gaccgccgca ttggttatct   4080
gggaaccgtg actgcgcccg cacccatcct gctctcttgg tgttctccat gctaacgttc   4140
cctccttttt gttctcctct acttgactct ctcctccctc gcttcaggtt ccgctgtacg   4200
ctctcaacca gcagctggtg atccacacat tcaaggcgct ggacatgggc ggcaccatcg   4260
tcatccacct gttcggagcc tactacggat tggcagcctc gctcatgatc agccgcaagt   4320
gagatacgca cgagggaggg aggcacacac ggcccgaggg agtggggcgc acacagaccc   4380
tgtgcccttg ccccttgctc agtgctcgtg tttttgccct tgctgctgct cccacaggca   4440
gccgctgcac ggcctggaca accccaagaa ctcgggcgcc tacctgaacg acatcttctc   4500
catgatcgga accatcttcc tcttcatcta ctgtgagtcc gcatgctgca tagagcgtcg   4560
cgtggttgcg ttgttgtgcc cgttgtgcag catcagtagc gccgatgtgc ccagatcccg   4620
cgcccgccct aggattaccc taccttctc  catctgaccc ctgctgcatc ctttctttct   4680
cattccaccg gccacagggc ccagcttcaa cggcgccctg gcgtccgtgt cggctggcca   4740
catggaggag gcgaccgatg ccaagaaggc cgcccaattc ctgtccatcg tcaacacgct   4800
gctgtcgctg ctgggcgccg gctatcggt  gttcgccacc tcggccctgg tgggcggccg   4860
cttcaacatg gtgcacatcc agaacagcac cctggccggt ggcgtggcga tgggcgccgc   4920
ctgcacgctg cgcctgacgc ccggtggcgc gctggctgtg ggcctgggcg cgggagccat   4980
cagcaccctg ggcttccagt acctcatgcc cttcctggac cgcaccatcg gactgggcga   5040
cacctgcggt gaggctgtca ttagttttgt gtgtgcacac aactctacgc ctctttcccg   5100
cccggccatc actgactgct gcgccctgcc attgcctgca tcgccgttgt ccccgcgccc   5160
aggtgtgcac aacctgcacg gcatccccgc catcgtcggc acgctggtgg ctggcctggc   5220
ggctctgggc cagcaccccg actacctgga gcacgacacc ggccgccagc agctgggcta   5280
ccaggtgctt gcgggcgtgg tgaccatggg catcgcaatc gccggcgcc  tgctaggcgg   5340 cttcgtggtg tcgtggttca accccgtgg  cgacgacccg ctgaccgtgc ccgaggtgag   5400
aaacggcggc cctgaggcgc tcccgttcgc ttgcttgttc cgcctacgcg ccgccttcgg   5460
```

```
ctgtaccttc ttgcgtcctt cttgttgctc acatgtgttt tgcccgtttt cctgcacgcc    5520
tgtctgcagc tgttcgacga tgggccctgg tgggagcacc agcgcgtgga gcccatgccc    5580
atctccacct ccatccacct cagcaacatg agcgcacacg gcaagagcca ccacaaccag    5640
tccgtcagcg gtgagtctcg gtctcgctcc ctgtggccgt cgcagcggct ggcatcagtg    5700
gccgtggcgg aagtggcttc ggttgtgcac gtgcgggctg cgcaacccag ggccaatccg    5760
ttgccgagtg tgacctccag cccacgcaac tcaccaactg cctcgcctgc tccgatttac    5820
ccgttctgcc gcagtgggcc agctcaaccc cattcgcgag ggccgcgaga tcgctgtgtc    5880
aggcgtgcct gccaccggcc agcgctccgt gggcgagatc gccgtgacca tgcaggccgc    5940
gcccgtgatg gcctcctcag cgcccgtgat gggcatgcac gccgccgccg ccaccccat    6000 cgatacgccg ctgttcgcgg acggtcacgc catggagaac gccgcgcgcc cggtgcagcc    6060
catggtggcc ggcgccggca acgtgtagag cggcagactc gttcggtgct cggcggacaa    6120
gacacgttag taaaagagat gaagtaagac gctgcggttg cagtcggcgg gggcagcggc    6180
tccgcggccg actgcgtgaa ctgatgaatg aatgagtgag gcggagccgg aagccaggaa    6240
cgcttgggag tcctggcaat ggtttgtgcc ttgaggctcg gcttggcttg cgtgagcgag    6300
cgtgcagagt gaggcgcgcc atgagcgcgt cgcctttgtc ttgcggtatt gtgaattgac    6360
ctgcttgtgg cttgggccgc gttggggatg tccggaagtg cgtccacggc tatgatcggg    6420
gtgggttacc catggtcgtg ggtgtctcta tgagcgctga agcgcaactg ctgctgggcg    6480
gagttgaaac tgctgagaag tccgtgggga gagcgtgttc acacacgaac acacaaatac    6540
acacatggtg tgcgtgtgca ctgattcttg cccgtatggg ccctgggatt gtagcgccag    6600
tgggagttgt tagggcgtcc ctgagagatt tgtgcacggc gcatatgagg cggcagcagg    6660
aattccccgc cgcgccgtac gcgtgggtgg tcggacagat ggtggcagtc gcaggcagta    6720
actagcgttt ttgttttgtgt ttgtgcgcac gccctgtgta ctgagttggc caccgcaggg    6780
tggccactgt acggtatttt acgagtgcca gggctgcacc agtcaggctt tcagttacac    6840
atggactaga tagcattaca cacggacggt acctgagtac caagaatcaa gctattagca    6900
atattacgaa tgtcgggaac cggattgggc gcacgtacac atcattagaa gtccgcatgt    6960
gtgacgtgtg tatggcatcg ggatgcaagg aaatccatgt gcttgccgga ctgtcggttt    7020
gagtgcatca tagcggattc ccatgcaata aggcatttgc ggcggcttgc tagaccacat    7080
actgctgctg ctgcacggtc aaggcacggc agcggcatgc aggggttagc atgcggaagg    7140
catttgtgtt actcaggctg tccgcgcatg ggtttgtctt ggtgtggtga cggcattgtg    7200
gtaatatcgg gatggcatta gctgcaagca gcaaaagcat gatgctagat agcaagcacg    7260 gatgtggcg acagtgttga agcaaacacg tttggcaggg ttgtggatga gttgactgcg    7320
caggtcgttg caaaccgttg aggcaacagt tcggtttgcg gcagtcggta gcatcaagtt    7380
catggctaaa taggcgagcc ggcgattaca tcgcatctac ttacgtgcgt gacctacgtg    7440
gtacatggcc cataccacaa ttacacatcg aacaggcaca tcctcaacat actgtaacat    7500
actaacattc cccaggagac gcgtgcgtca gcccgtttgt gaagtgcacg ctcacggggc    7560
ccaaccccac ggcaccatgc tccgagcttt gcgccctgct tggcctttcc cggctactca    7620
cagatgcagc ggagccatga cgcagcacca gctgcacagc acggcattgc ttccagcacc    7680
ccctcgaagg ttccaagtcc cccgtacatt gcaactcgcg gcgacagcgg cagcctgcca    7740
cgggacggcc ccgactccct ccaggcgctc gcagcacctt ccagctaccg cccagccaca    7800
```

```
cgccccgcca tcacacgcgc tgcaccgcat ccgcacgccc gcacaccacc accgtgcgca       7860
tttcgtttct tgagcatct tcggtaacca ccgcaccgca gcaccgcaa ccatcacctt         7920 gccgcgccct caaagtcc                                                    7938
```

```
<210> SEQ ID NO 6
<211> LENGTH: 54
<212> TYPE: DNA
<213> ORGANISM: Chlamydomonas reinhardtii
<220> FEATURE:
<221> NAME/KEY: misc_signal
<222> LOCATION: 54
<223> OTHER INFORMATION: transcript initiation A

<400> SEQUENCE: 6
acgtgcaggg ctagtgacga cggaggtgtg gtagggttag ccggcggtga ggga            54

<210> SEQ ID NO 7
<211> LENGTH: 23
<212> TYPE: DNA
<213> ORGANISM: Chlamydomonas reinhardtii
<220> FEATURE:
<221> NAME/KEY: misc_feature
<222> LOCATION: (14)...(23)
<223> OTHER INFORMATION: Shine Dalgarno region
<220> FEATURE:
<221> NAME/KEY: misc_signal
<222> LOCATION: (21)...(23)
<223> OTHER INFORMATION: translation start codon

<400> SEQUENCE: 7
cggaactcag gccggcaacc atg                                              23

<210> SEQ ID NO 8
<211> LENGTH: 574
<212> TYPE: PRT
<213> ORGANISM: Chlamydomonas reinhardtii

<400> SEQUENCE: 8

Met Gln Ala Leu Pro Pro Lys Ile Pro Ala Ser Val Ser Gly His Gly
1               5                   10                  15

Thr Gln Ser Arg Arg His Ser Leu Asp Trp Ser His Ile Gly Leu Pro
            20                  25                  30

Ser Arg Glu Thr Gln Leu Arg Ala Gly Phe Val Pro Ser Ala Ala Val
        35                  40                  45

Val Ile Val Ile Phe Val Gly Leu Phe Phe Gly Leu Thr Gln Tyr Thr
    50                  55                  60

Glu Leu Gly Thr Asn Ala Gln Glu Glu Val Asp Arg Phe Tyr Lys Tyr
65                  70                  75                  80

Leu Val Asp Val Asn Ile Met Val Trp Ile Gly Phe Gly Phe Leu Met
                85                  90                  95

Thr Phe Met Arg Arg Tyr Gly Tyr Gly Ala Val Ala Leu Asn Tyr Phe
            100                 105                 110

Ala Ser Ala Leu Met Phe Leu Glu Ala Ile Leu Met Ile Gly Ala Thr
        115                 120                 125

Gln Gln Val Phe Trp Asn Tyr His Arg Thr Lys Ile Gln Ile Asp Ile
    130                 135                 140

Ala Leu Leu Ile Asp Cys Ala Phe Cys Ala Ala Ser Gly Met Ile Ala
145                 150                 155                 160

Phe Gly Ala Ile Ile Gly Lys Ala Thr Pro Thr Gln Leu Leu Trp Leu
                165                 170                 175
```

-continued

Leu Phe Trp Gln Val Pro Leu Tyr Ala Leu Asn Gln Gln Leu Val Ile
            180                 185                 190

His Thr Phe Lys Ala Leu Asp Met Gly Gly Thr Ile Val Ile His Leu
        195                 200                 205

Phe Gly Ala Tyr Tyr Gly Leu Ala Ala Ser Leu Met Ile Ser Arg Lys
    210                 215                 220

Gln Pro Leu His Gly Leu Asp Asn Pro Lys Asn Ser Gly Ala Tyr Leu
225                 230                 235                 240

Asn Asp Ile Phe Ser Met Ile Gly Thr Ile Phe Leu Phe Ile Tyr Trp
                245                 250                 255

Pro Ser Phe Asn Gly Ala Leu Ala Ser Val Ser Ala Gly His Met Glu
            260                 265                 270

Glu Ala Thr Asp Ala Lys Lys Ala Ala Gln Phe Leu Ser Ile Val Asn
        275                 280                 285

Thr Leu Leu Ser Leu Leu Gly Ala Gly Leu Ser Val Phe Ala Thr Ser
    290                 295                 300

Ala Leu Val Gly Gly Arg Phe Asn Met Val His Ile Gln Asn Ser Thr
305                 310                 315                 320

Leu Ala Gly Gly Val Ala Met Gly Ala Ala Cys Thr Leu Arg Leu Thr
                325                 330                 335

Pro Gly Gly Ala Leu Ala Val Gly Leu Gly Ala Gly Ala Ile Ser Thr
            340                 345                 350

Leu Gly Phe Gln Tyr Leu Met Pro Phe Leu Asp Arg Thr Ile Gly Leu
        355                 360                 365

Gly Asp Thr Cys Gly Val His Asn Leu His Gly Ile Pro Ala Ile Val
    370                 375                 380

Gly Thr Leu Val Ala Gly Leu Ala Ala Leu Gly Gln His Pro Asp Tyr
385                 390                 395                 400

Leu Glu His Asp Thr Gly Arg Gln Gln Leu Gly Tyr Gln Val Leu Ala
                405                 410                 415

Gly Val Val Thr Met Gly Ile Ala Ile Ala Gly Gly Leu Leu Gly Gly
            420                 425                 430

Phe Val Val Ser Trp Phe Asn Pro Arg Gly Asp Asp Pro Leu Thr Val
        435                 440                 445

Pro Glu Leu Phe Asp Asp Gly Pro Trp Trp Glu His Gln Arg Val Glu
    450                 455                 460

Pro Met Pro Ile Ser Thr Ser Ile His Leu Ser Asn Met Ser Ala His
465                 470                 475                 480

Gly Lys Ser His His Asn Gln Ser Val Ser Val Gly Gln Leu Asn Pro
                485                 490                 495

Ile Arg Glu Gly Arg Glu Ile Ala Val Ser Gly Val Pro Ala Thr Gly
            500                 505                 510

Gln Arg Ser Val Gly Glu Ile Ala Val Thr Met Gln Ala Ala Pro Val
        515                 520                 525

Met Ala Ser Ser Ala Pro Val Met Gly Met His Ala Ala Ala Ala Thr
    530                 535                 540

Pro Ile Asp Thr Pro Leu Phe Ala Asp Gly His Ala Met Glu Asn Ala
545                 550                 555                 560

Ala Arg Pro Val Gln Pro Met Val Ala Gly Ala Gly Asn Val
                565                 570

<210> SEQ ID NO 9
<211> LENGTH: 31
<212> TYPE: DNA

<213> ORGANISM: synthetic oligonucleotide

<400> SEQUENCE: 9
ctaaaggatg ttgacacaat gtgatttctg c                             31

<210> SEQ ID NO 10
<211> LENGTH: 30
<212> TYPE: DNA
<213> ORGANISM: synthetic oligonucleotide

<400> SEQUENCE: 10
ccttggatgt ggtagccatc tctcatgctc                               30

<210> SEQ ID NO 11
<211> LENGTH: 3999
<212> TYPE: DNA
<213> ORGANISM: Chlamydomonas reinhardtii
<220> FEATURE:
<221> NAME/KEY: misc_feature
<222> LOCATION: (720)...(819)
<223> OTHER INFORMATION: n=a, t, c or g
<220> FEATURE:
<221> NAME/KEY: misc_feature
<222> LOCATION: (3790)...(3989)
<223> OTHER INFORMATION: n=a, t, c or g

<400> SEQUENCE: 11

| | |
|---|---|
| ctaaaggatg ttgacacaat gtgatttctg cccagtgctc tgaatgtcaa agtgaagaaa | 60 |
| ttcaaccaag cgcgggtaaa cggcgggagt aactatgact ctcttaaggt agccaaatgc | 120 |
| ctcgtcatct aattagtgac gcgcatgaat ggattaacga gattcccact gtccctatct | 180 |
| actatctagc gaaaccacag ccaagggaac gggcttggaa taaacagcgg ggaaagaaga | 240 |
| ccctgttgag cttgactcta gtccgacttt gtgaaataac ttaagaggtg tagaataagt | 300 |
| gggagcttcg gcgacggtga ataccacta cttttaacgt tgttttactt attccattac | 360 |
| ttggaggcgg gactctgtcc ctgcttctag ctctaagacg gcttttgcac gtcgatccag | 420 |
| gtggaagaca ttgtcaggtg gggagtttgg ctggggcggc acatctgtta aaagataacg | 480 |
| caggtgtcct aagatgagct caacgagaac agaaatctcg tgtagaacaa aagggtaaaa | 540 |
| gctcatttga ttttgatttt cagtacgaat acaaactgtg aaagcatggc ctatcgatcc | 600 |
| tttagccttt cgggatttga agctagaggt gtcagaaaag ttaccacagg gataactggc | 660 |
| ttgtggcagc caagcgttca tagcgacgtg cttttgatcc ttcgatgtcg ctctcctatn | 720 |
| nnnnnnnnn nnnnnnnnnn nnnnnnnnnn nnnnnnnnnn nnnnnnnnnn nnnnnnnnnn | 780 |
| nnnnnnnnnn nnnnnnnnnn nnnnnnnnnn nnnnnnnng gacgcggggg tgagagtggg | 840 |
| gttggcacgg gggagtgtgt gcgtgggcgc gccagcgagt gcgcgagtgt gaatgctgaa | 900 |
| ttgttaacac tgcaccctgt acgtatctac tatgtatacc ttacgcaacc ttaggaaacc | 960 |
| tcttggaatt aacttacggg aatgaaaaac ctgttgagct tgactctagt ccgactttgt | 1020 |
| gaaattactt agaggtgtag aataagtggg agcttcggcg acggtgaaat accactactt | 1080 |
| ttaacgtgtt ttacttattc cattacttgg aggcgggact ctgtccctgc ttctagctct | 1140 |
| aagacggctt ttgcacgtcg atccaggtgg aagacattgt caggtgggga gtttggctgg | 1200 |
| ggcggcacat ctgttaaaag ataacgcagg tgtcctaaga tgagctcaac gagaacagaa | 1260 |
| atctcgtgta gaacaaaagg gtaaaagctc atttgatttt gattttcagt acgaatacaa | 1320 |
| actgtgaaag catggcctat cgatccttta gcctttcggg atttgaagct agaggtgtca | 1380 |
| gaaaagttac cacagggata actggcttgt ggcagccaag cgttcatagc gacgttgctt | 1440 |

```
tttgatcctt cgatgtcggc tcttcctatc attgtgaagc agcattcacc aagcgttgga  1500
ttgttcaccc actaataggg aacgtgagct gggtttagac cgtcgtgaga caggttagtt  1560
ttaccctact gttggaccga ttccgccata gtaattcggc tcagtacgag aggaaccgcc  1620
gagtcagata attggtaatg cccttgtctg aaaagacaat ggggcgaagc taacatctgt  1680
agtctaatga ctgaacgcct ctaagtcaga agacgtgcta ggtgcggagt cacttaccca  1740
atgatgtcac ccgactaagg atacatccgc ctgtgcggat gctggagcat acccgttggt  1800
tcccctgtta ggtccacatg gccgaagcag gcgccaagca tgacaattcc actcgtcatt  1860
ggggtaaatc tctgtagac gactttgttg caactgggta ttgtaagtgg tagagtggcc  1920
ttgctgctac gatccactga gattcatccc gtgttgctaa gatttgtcac tgcccttcgg  1980
ggcaacccct cctcctctcg gagcgacagc tccagggagg gccctctctc tctcttccaa  2040
gtggtgtagc tgagctgagc gcgtgccaac gccgccgaat ccgtctaagt gcccacatgc  2100
gtgtgcatgc actgcccctc ctcccccaca cagccaaagt gctcaaggta ccttccctgt  2160
gtgtgtgcga gtgagagcaa cagcatgcat gtgcccttac ttaggcggcc tagtgtggta  2220
tgtgtgtatg cgtgtggctt agtggccagt tcgactctgg cgtggaagct atcttctaag  2280
gcagtggcgc atgtgtgctg ggtgggtggg tgggtgggta gaggttaggt agggtagggc  2340
aaggtgggta ggtcggtagg taaaggttcc gtggtgctgt ttgattttag atagtccagt  2400
gggtggcgtt tatgtatgtg gaaatcgctt ttcaggattg ggtatagctc cagggagggt  2460
gagtgggttg ggagtgtgtt gggagcccct gccgtgtcac tgggcctgtt gggccaaggt  2520
accagcactt gggtggcgtg gccatagct ggttgtcaaa cggggtttga aggggtttta  2580
cggggtttta gcggggttat aacgccggcc gtccctagag gggtcagtaa actctaccaa  2640
cgtgctggac agacctcctg tgacatggga accttagtgg gggtggtggg tgggggtttg  2700
ggtgggttgg gcaccttggg tgtttgaacc ccggggtttt cggggttat cggggttttt a  2760 gccgtagcgt gcagtatgac atgaggaaaa gtgcgctgac tggccaggcg tgcttgggt  2820 ggtgtagggg tgacgtgggt tgattttag ggtgagttga tgcctggagg gggtggtcac  2880
cttgggaggg gttttggggg gttttacgcg tgtaccacga cgtggggcgg tcggattacg  2940
tgtattaaac atgcttaatt aacgtaatta gtttggttta gggttgtggg gttcccccct  3000
tagggttttt ggggtcgggg gtgtgtgggt gggggggtgt ggggttttgg tcaaacgttg  3060
gtcaaacgtt gcctggtcaa agtttgaccg gccttagtca gcgcgttgtt gtgccaatag  3120
gctcctgtct ttttcttatg tgtcttatgt gttgtgttag ataaggtttc ttatgtgtgt  3180
gtgtgtggct gttgggttag ataagacata taagggtttc ggggttttgg tgccctgtgc  3240
cttgttccgc gggtcccaac gtgtcccct tgtgctggca tggtgttggg agtgtgtgcg  3300
atgtgttgga agcgttgggg gtgcttggag tgcagtttgg tgtgtgtggt gtggtgtgga  3360
gttggtcaag ggtgtcagtc cccttggcac gctagcaacc ctaccccata tccacccct  3420 ggccagctct gccaccctcg cccacgcgca tgcactcaca gcacgtcaaa cgagttccca  3480
tttcactttg gcatgtatgg ggaggcatgg ggcagctccg ggcggggatg gcaccatggc  3540
ggtggtggta ccgtgtgctc gggtcctgcc tttggctctg cttgtccatg acgtacggct  3600
ctgggtatct tccatgcccg taagttatgg ccctaaggta ccctaaggta ccctaaggta  3660
cccacgcgtg tgccctctag ggtacagggg taacacttgc gcatacacac acgcgcgcac  3720
acacgcacac acacgcacac actcccaaca gcatgccagc acaagggga cacgttggga  3780
```

-continued

```
cccgcggaan nnnnnnnnnn nnnnnnnnnn nnnnnnnnnn nnnnnnnnnn    3840
nnnnnnnnnn nnnnnnnnnn nnnnnnnnnn nnnnnnnnnn nnnnnnnnnc ctatcaactt    3900
tcgatggtag gatagaggcc taccatggtg gtaacgggtg acggaggatt agggttcgat    3960
tccggagagg gagcctgaga gatggctacc acatccaag                          3999
```

<210> SEQ ID NO 12
<211> LENGTH: 24
<212> TYPE: DNA
<213> ORGANISM: synthetic oligonucleotide

<400> SEQUENCE: 12

```
cgactgaacg cctctaagtc agaa                                             24
```

<210> SEQ ID NO 13
<211> LENGTH: 25
<212> TYPE: DNA
<213> ORGANISM: synthetic oligonucleotide

<400> SEQUENCE: 13

```
gcctgctttg aacactctaa tttac                                            25
```

<210> SEQ ID NO 14
<211> LENGTH: 5879
<212> TYPE: DNA
<213> ORGANISM: Chlorella
<220> FEATURE:
<221> NAME/KEY: misc_feature
<222> LOCATION: (423)...(472)
<223> OTHER INFORMATION: n=a, t, c or g
<220> FEATURE:
<221> NAME/KEY: misc_feature
<222> LOCATION: (2031)...(2441)
<223> OTHER INFORMATION: n=a, t, c or g
<220> FEATURE:
<221> NAME/KEY: misc_feature
<222> LOCATION: (4827)...(5514)
<223> OTHER INFORMATION: n=a, t, c or g

<400> SEQUENCE: 14

```
cgactgaacg cctctaagtc ggaagccatg ctaggagcgg ggtcatctgt cccaatgacc     60
gtcacccgac taccaatagg ctggattctt tccagtccag gagcatatcc gatggatccc    120
tcggctcagg tcacacgcct gggtcggggc catgcatgac aattccactc gctcattggg    180
gtaaatcctt tgcagaccac ttagctggaa cgcggtattg taagcggtag agtggccttg    240
ctgctacgat ccgctgagat tcagccgttg ttcttacgat ttgtcaccct cctgctttgc    300
tggcggtcaa gggtgggctt tgggtttggc ggccgcatgg gggcaaaccg cttccaaggt    360
tagtccaggg tggggccttc gggcttggaa gccttggccc aatcggggca gagattggca    420
aannnnnnnn nnnnnnnnnn nnnnnnnnnn nnnnnnnnnn nnnnnnnnnn nntggcaggc    480
taaaacccat ggcggctcgg ggggtggtc cagggtgggt caccaccatc cccatcggtc     540
atttttaagc aaacgacgtt aaaacgaacg atttcatggt cttagggcgg gtcagtggtc    600
cagggtgggt caccacgggt ggtgggccat ttacacgatt tcaatcggtg gcagcgaatt    660
gatactccca accacgaggt gaaatattgg aattcatatc caagggcgt ggattcccta    720 ggcctgcacc gcacaccgtt tgctgcaccc agggaggggc tcgaggggg cctcggggca    780 ggaaggggg gctgccttgg tcaggggggt gggagcccgc tcaggtgtta cagtcacccc    840
gctatgatag gccgcgtgag cagaccttgg gcagggggca cacgtgatca agggggcatca    900 agagaggggg tggaccatgg agcaccctct ccatggctcc gaccacccctc cccccagctg    960
```

```
agcgtcccag ggtcacccca ccctggcccc gctccccgtc ctgccggaca cgcaaccccc   1020
acaacgtggt gggggggcgtg gggatcctta cagggcctg ccaggccgac gggtgccgat   1080
gctggtgcgg gctcccggcg gcaggcagcg ccgccaccgg gcgctcagat ggcgtgtgta   1140
gcaggactag cctccgctat cccgctgatc gctctatctg actatggctc tctctgctaa   1200
ggtataagcg tgcttacaac ggcgcctgca ccccagcaga aaggcccagg ggcaggcgga   1260
aacaccagca aaaggggcta acagcatag catgcacgcc gcgccgtcgg cgccgtcgcc   1320
agcgccggcg ctgcagcgct gctcctacta cactgccccc ctccaggaat aggcatcgtc   1380
ctcgagccgt aaccgcgtaa gctgccgagc agaaacaatg cggtcaaagc agtgtagaga   1440
gagagtaggc gcaaggaaca gaagtagaag tacatcgagg gacatacgaa gcagggggaat  1500 caagcagata caagtcgggg ggagcgccgc gcaggggcag acgccgaggg ggcgctgcca   1560
gcagcaacct tgcggccagg caaactccac catgggcagc agctcatccc agtccgtctg   1620
gtccgcacac acgaaatggc gcagcacctc cccaaccagc cgattcatcc gctcagcctg   1680
gccgtcggtc tggggatggt aagccgtcga tgtgttcagg cgcgtccgca tcagctgcat   1740
aagccgctgc cagaatgcgc tcatgaactt ggggtcgcga tcactcacaa ccacccgtgg   1800
ccaccccatc tgcgacagca cccgctcatt gaaagcgcga gctgtcccct cagcatcggg   1860
acgccgcatc ggaaccagct tcaccatctt ggtgagcagg cagacgcaag tcaggatgaa   1920
tcctttccat ccggcgtctc cggcaaaggc ccaatgaatc catgcccacc acctcccagg   1980
gacaccaggg atgggaagtg gctgcagcaa gccaggtgcc gctccacggc nnnnnnnnnn   2040
nnnnnnnnnn nnnnnnnnnn nnnnnnnnnn nnnnnnnnnn nnnnnnnnnn nnnnnnnnnn   2100
nnnnnnnnnn nnnnnnnnnn nnnnnnnnnn nnnnnnnnnn nnnnnnnnnn nnnnnnnnnn   2160
nnnnnnnnnn nnnnnnnnnn nnnnnnnnnn nnnnnnnnnn nnnnnnnnnn nnnnnnnnnn   2220
nnnnnnnnnn nnnnnnnnnn nnnnnnnnnn nnnnnnnnnn nnnnnnnnnn nnnnnnnnnn   2280
nnnnnnnnnn nnnnnnnnnn nnnnnnnnnn nnnnnnnnnn nnnnnnnnnn nnnnnnnnnn   2340
nnnnnnnnnn nnnnnnnnnn nnnnnnnnnn nnnnnnnnnn nnnnnnnnnn nnnnnnnnnn   2400
nnnnnnnnnn nnnnnnnnnn nnnnnnnnnn nnnnnnnnnn ngatctgcgt gcatgcaggg   2460
tttggcaact gtgatggcaa caccgccaac ggctgcgaga acccgttgag ctcaaatccg   2520
aattgcggcc tgtgcggctt cacttgcccc tctggcttcg gctactcctg cacgaacaag   2580
gcgtgcacga aagacataag ctgcggcgat tttgtcactt tcactggtgg tgcgagcaac   2640
ctcacacaca ctgtcaacaa cgttggtggc gtcaatctga cgctaactat caattcgttc   2700
tcagctgtga gtactgcaag gcatttgtca caatcttgga gttgcaaatg ctatggcctg   2760
accgctcctg cccttgccct ccgcagcccg atgagtacat tttgtatcgt ggcgacaccg   2820
gcgccgaaat tttccgagtg ttgaccggga ctgagggcaa accctcccgt ggggtcagag   2880
ataggggatg cttgctcgac aagaacggta attcgtgcga ggcaaccgag tgcagagtcg   2940
gcaacggcac cgtcaccagc aacggcccct gtgtggcacg cctggctccc acatctggtt   3000
gccccaagga gtgtctgtgg tttgcctatc gcgacgtcct ccccaacggg atattcacta   3060
tccctcgtcc cgctggtgtc tctacgttct tgttgcaagt taatggtgcg tgcccctcca   3120
cagggtggga ggtgacagtt ggctgcacaa atatatgatg tgcaactccc gttttggttt   3180
gagtttgtca ctcgctttgc cgtctgttcg tcccgttgcc attgaaatgc tttcaatcgc   3240
ccagcaaatt agggtttagg gtttaataat cagcaatagt ggtggcacag catgcaaagc   3300
```

```
acagcattgc caggtatgaa tggagggaac tatgtactat cagctgagca ggatctgaga    3360
cctgctacac catggctcca gccaccctcc ccccaagctg agcgtcccag ggtcacccca    3420
ccccgggccc actccccgtc gtgccggaca cgcaacccccc acagcgtggt gggggacgtg   3480
gggatcctta gcagcttagg cctgccaggc cgacgggtgc cgatgctggt gcgggctccc    3540
ggcggcaggt agcgccgccg ccgggcactc aaatggcatg gggcacacgg gcccccatgc    3600
ccgcacatct cccaggcaca tgaaaatacc agaaggctgc acatgtaagg gtgcaggcag    3660
gagtgcaaag tggcctgccg cagcggtcgg ctgtgccatt actcaatcaa ccgccgcttc    3720
cgtgccgggc ttggcgttcc catgccaaca tgccggcgtg ccatcgcgca tggtgaaggc    3780
ctggaggcgg ggcgcagctc cgacgccacc ttggcgcgtt gcccagcgcc ataccgtcgc    3840
cgtgaccacg ccgcagctcc agccgcccag ccgcctatcg cctgcttggc gcggcctggc    3900
tggccacacc ccaccccat acctaccagg aggtcaggtc cctggctggc tgctcctggg    3960
caagcaccaa acaccatggt gcagcctgta gatgcgttgc ctgcccccctg gggcctccat    4020
cctctgctat agtgcatgcc cctgccatc ccaccgttcc ttacacaggg cgctccaccc    4080
ttccctctcc tgtcaactgg tggcccgtgg ccctccctac ttgcagcaaa ttgtgtgcgg    4140
tttgttccag aaataccatt taagtttact atgacttgca atacacctttt tcacgtgccg    4200
tgctgccatg gttgagcaga ggaggtggaa gctgaaagca gagaatggcg gctcccggtc    4260
gacacggttg agtttccacg atttgcagac ggctggaact ccaagcttgc ccagtgaaag    4320
gttctctgat tggccttggc ccgactggtt acagttggga cgcctgcaaa ggcgtgtcag    4380
ttggatggag cctggtaact gatgagtgac cgagcgcttc cgagtgctgt gaccggcggc    4440
tgaatgttgc tgctggtctg gctcaatcgg ttgcgtctca atgactgttg cttggggttg    4500
agttcaagtg acgtgggct gcctctgtgc cttttctgtg ccagagcgta gccacgttg    4560
aggagcttgt atcgttacac gatgtgcaag cttatcgcca aacccactgc cagaacagtc    4620
ggtgtctgtt cggatccgcc tctcatgggg cgttgaacct tgagcggcat cgatctgctg    4680
gcggcacagc cgcccctgcg ggagtccatc tcagacgagc gtttcgacgc cctgggtttg    4740
ctggctccga atcgctgggt gtgtgctgga agaagcctca gagaggattc gaggaaagag    4800
agcctttccg gcgtcggcgc tctcttnnnn nnnnnnnnnn nnnnnnnnnn nnnnnnnnnn    4860
nnnnnnnnnn nnnnnnnnnn nnnnnnnnnn nnnnnnnnnn nnnnnnnnnn nnnnnnnnnn    4920
nnnnnnnnnn nnnnnnnnnn nnnnnnnnnn nnnnnnnnnn nnnnnnnnnn nnnnnnnnnn    4980
nnnnnnnnnn nnnnnnnnnn nnnnnnnnnn nnnnnnnnnn nnnnnnnnnn nnnnnnnnnn    5040
nnnnnnnnnn nnnnnnnnnn nnnnnnnnnn nnnnnnnnnn nnnnnnnnnn nnnnnnnnnn    5100
nnnnnnnnnn nnnnnnnnnn nnnnnnnnnn nnnnnnnnnn nnnnnnnnnn nnnnnnnnnn    5160
nnnnnnnnnn nnnnnnnnnn nnnnnnnnnn nnnnnnnnnn nnnnnnnnnn nnnnnnnnnn    5220
nnnnnnnnnn nnnnnnnnnn nnnnnnnnnn nnnnnnnnnn nnnnnnnnnn nnnnnnnnnn    5280
nnnnnnnnnn nnnnnnnnnn nnnnnnnnnn nnnnnnnnnn nnnnnnnnnn nnnnnnnnnn    5340
nnnnnnnnnn nnnnnnnnnn nnnnnnnnnn nnnnnnnnnn nnnnnnnnnn nnnnnnnnnn    5400
nnnnnnnnnn nnnnnnnnnn nnnnnnnnnn nnnnnnnnnn nnnnnnnnnn nnnnnnnnnn    5460
nnnnnnnnnn nnnnnnnnnn nnnnnnnnnn nnnnnnnnnn nnnntaccac atccaaggaa    5520
ggcagcaggc gcgcaaatta cccaatcctg acacagggag gtagtgacaa taaataacaa    5580
tactgggcct tttcaggtct ggtaattgga atgagtacaa tctaaacccc ttaacgagga    5640
tcaattggag ggcaagtctg gtgccagcag ccgcggtaat tccagctcca atagcgtata    5700
```

```
tttaagttgc tgcagttaaa aagctcgtag ttggatttcg ggtggggcct gccggtccgc    5760
cgtttcggtg tgcactggca gggcccacct tgttgccagg gacgggctcc tgggcttcac    5820
tgtccgggac tcggagtcgg cgctgttact ttgagtaaat tagagtgttc aaagcaggc    5879

<210> SEQ ID NO 15
<211> LENGTH: 43
<212> TYPE: DNA
<213> ORGANISM: synthetic oligonucleotide

<400> SEQUENCE: 15
cgcgctcgag cgggtgtgat gtgagaacca atactttgta gcg                       43

<210> SEQ ID NO 16
<211> LENGTH: 37
<212> TYPE: DNA
<213> ORGANISM: synthetic oligonucleotide

<400> SEQUENCE: 16
gccgctcgag atcgagttat tgatactatt acaaaag                              37

<210> SEQ ID NO 17
<211> LENGTH: 812
<212> TYPE: DNA
<213> ORGANISM: Paramecium bursarium Chlorella virus 1

<400> SEQUENCE: 17
cgcgctcgag cgggtgtgat gtgagaacca atactttgta gcgttttcaa aataggatcc     60
gtatcctttt ttttgactgg tacgcaaatc gcttttctgt cgttcgtttc gttttttgag    120
cattgatctg cgtgacctct gcaatacccct ttgcacacag cggatccgta tcctttttt    180 tgactgcgta cgaatcgctt ttctgtcgtt cgtttcgttt tttgagcatt gatctgcgtg    240
acctctgcaa tacccttgc acacagcacg tctgccacaa ggtttgttcg tactcgtcaa    300 cccttttgcat ttcgctttcc cagaaccgag aagtgcgtgt ttatcaagga tgtcatcttt    360
gtattgttca aggagtttcg tgtaattcaa gccgtaatct cgcgcaacac acagtagaac    420
gtcttctatt gcggaaccca cgatggtccc ggtaaattcc tcgatggctt tcgcaccatt    480
cacaacgttt gacaacgtct tcaaaaagct tccttccatg ctttaatttt aattactaag    540
gatgacccgt tggttaaatg tgtagtgcgt caatatacaa atgtcattta tttgttttcg    600
caaggctcgt atcgacaaga tattttata aggatgatac tgatattaat gtcttatgga    660
atttgaacac tacgatggaa ggaaaaatgt caaggtggaa gttatctagg aaacgtcttg    720
ggttgtcaag accttacaat cgtaaaaatt gcgtgtaaaa atctgaaaaa aaatcttttt    780
gtaatagtat caataactcg atctcgagcg gc                                  812

<210> SEQ ID NO 18
<211> LENGTH: 1089
<212> TYPE: DNA
<213> ORGANISM: Chlamydamonas reinhardtii

<400> SEQUENCE: 18
tgggcacgcg gcaacgaatg gccaactcgg tttgatggaa atccttcttg actgcggcac     60
atttgatgac ccgctacaac aaagaaaagc atgataggct gataccagag aggcacggca    120
gtcgtgtgat gctgcagtgt gctgtggccc tgaccactca tgtttcttac ttagagagta    180
gtcctggaga gtcagagagg cgtgcttgcg atcctcgcat tctttttgcg tgcaatgcat    240
```

```
atccatagac catacagttc atatcgtaca gttgctacca ggagtttatc agggtcccct      300
catcttcagc aggggaaccc ctgttatata gcaccctcgc caatggggcg actgaccgac      360
catccaaccg gcttacagct ccgcgcgggg acatcttgcc ctgattggtg tgggcttgca      420
ttggccaggc catagcgacg cgagccagca taattgcatc tgttgtcaga agctgcttcc      480
tagtccttag cacctccaac ctgcgggcgt caaggcgcct attgtaactg cattcgtgat      540
ctactccata cacgcccacc gcccaaggcc gcactactgc cgggatgcaa ccaagcagcg      600
caaaactcct gcaggccaag cctaataata atggtgccga gtactcagcc agcctcaatc      660
cctatccagt gatctgcctc agtaccgatc ggcgatcgtt attggattct accgcatcca      720
cggaatccat ggtatccacc gctacccaag cggcaacctc cacacctggg gtgtgtgccg      780
gagtgcactt tggttccatg cctagccaat gcggaccacg tgcggaccgc tacttcgtaa      840
gcactgccgt caaaagcgag cacctttatt gctgacttcc aactctgcgc aacccgcgcc      900
aacatgatag tactgtacag cagctccata cactgcgacg ccgccagtgg catcagctcg      960
cgctagcatc aactccacac tacaaagtcc ttgacggagc ggcctgcctg tggattccag     1020
gacgcacttg gcgtagggtg ccatcctcct cccctttgggg cacgtcaaca ataacctcag     1080
cgcaccaaa                                                             1089

<210> SEQ ID NO 19
<211> LENGTH: 1025
<212> TYPE: DNA
<213> ORGANISM: Chlamydamonas reinhardtii

<400> SEQUENCE: 19
ggcgcgagcc actgagccag gtacccgaca agggccgtgt gcgcggctcc tcgattaagc       60
tcggcctgga aggcttttacc cacacccatt ttgacacggc cacacagccg gaggtggtgc      120
ctcaagacac gagcacggtg cgcgtcgggc cgcccggccc tgcccttcac gcgtgcagct      180
ttcctcactc tggccggtat tacagccatc actttgggag ttgggactat gcttctcacc      240
accctctgct cgggcttgta ctaggaattc agctctcccc atcctggccg ctcccggagt      300
cccgcgtgcc tcctccccag ggcgcagacc gccacgcagc ccccgactg cgcggcccag       360 cccgtccggt gctttcgctc gtgagcttcg cccgcaggtc cgtgttgtaa gccatgcaat      420
ctgcgcgtgt ggcacagtac acatactggc gtctggcact ctggcgagaa gtgctgcggc      480
gctggcccga agacagacac tgaccccctc ccatagtcca gagcctgacc ccttcgaatg      540
ctaacgcccc aatccagcca ccaaagcttg aatgcgacac atcggcaact tctcgagaac      600
cccagtgcgt ccgtgcgagg atttcgcagt gcgactgcca gcaactaggg tccccggacc      660
tcaacctgaa gtttcctgaa cgtttatgat gttgagctat agcgcatata accagctatt      720
ctatcgattc ggcaaccata gccgacgacg tctgagtttc gcctaagacc ttttttcctac     780 ctgggtccct gccttccgtc gggagcaagc ttatagtatg gacttgtctt tccacctctg      840
atgcaaagcg cttgagcctg cgcgcgggcg cccgccagtc agacgccatg gcacgtgcg       900 cgctttcctc gtacacccca attgcgtcat gtgatagaaa tttctcacct gtccccgtga      960
gcttgtttta ccggttggtc gttgaccac acacctaatc gttcgctggc tagagcacaa      1020
caatg                                                                 1025

<210> SEQ ID NO 20
<211> LENGTH: 1020
<212> TYPE: DNA
<213> ORGANISM: Chlamydamonas reinhardtii
```

<400> SEQUENCE: 20

```
ggaccggcgg cgttatgcgg cacgacggcg tcaggggatc aggagggaac gcagaaccgg      60
agctgtggct gcggccatgg cagcggcggc ggctggtgac cgacgttctt gtgaggatgg     120
taaagggcga gcattcaaat gcgtgagcgt gaagaactgc agtgtgtgga ttggggaggg     180
ggggccagat tccactagca cgttgtgtgc tgctggcagc agcacgatga ttgacgattg     240
gaaaacgctt gctcgtgagc ggctcgtgtg acgtgactag gggcgcattt tttgacagag     300
cgatccgaat gtatgcctat gatcagtaag ggcatacgtt gctgctgctt gggcgcgggg     360
gcctgctgcg ccagttgcat tgctgcctgc gtgtcaggcc cgttgggcgc ccattcgagt     420
ttggcgttcc gcattcatat cacacctact aagcgccac acattcacgc atcccagccc     480
cttgcccgga tctgaaccat actataatgc atcatgtttg acaagtgtct gtgtgtgact     540
gtcgtgactt aaaccatgag cgcgcgctgc cgggtgctga ttgcgagaag gctggacggc     600
ttcgcaggtg actggaccgc aggacagcgt gcttttactt tctggtacgg tacgaattgc     660
ttgacacctc cttgcacaat gaattgtcgt gtgtgcgcgc gtaacttcgt agatttgaaa     720
gtagtcttgt tgtgcgctcg cgtgtgattt gcgccccct gagtgatttc ctgtgaacag     780
ttcggacctt gaagttactt gtatgggcat atgggtaaac agcgatcttc agaggaccaa     840
cttcagtcag gggacggaag gcatggtgtg catcaggtgc gtgtgtgcgt gcgtgcatgt     900
ggtggacgga gattgggccg aggggaaaga aagcccccgc gccatgactg tgacggcggc     960
actgcaaagt gggcgcacgt ccagagccaa acaacggctg taacgatatt ccgaatgcca    1020
```

<210> SEQ ID NO 21
<211> LENGTH: 1003
<212> TYPE: DNA
<213> ORGANISM: Chlamydamonas reinhardtii

<400> SEQUENCE: 21

```
ccgcgagtcc atcgagaatg ctagtgggct cggcgcagac tctccgccaa acaccccgca      60
taccgtgctg tttggcgcct ccgcttcgc acgagccctc gacacaccgc gccactaggg     120
ttgtcgaaac ccaccgtgac tcacacagcg gtgtgccgcc cctgactagc aaccgataaa     180
gcactgtgac tgccatattg ttttccatcg ctttcactgt cgccgctgcg caaggccagc     240
cgcgcacaaa agcgcgaaat ttttggcgca gggaaaagcg tcgttgtcta cgtttgacaa     300
gcctttatgt tatgagcaat acagcgatct actggaacga ccgcaatta cccaccatag     360
cggcatcctt ttactccagt caactagggc tttgaggcac gcggcaattt tgctcgacaa     420
caaagagcgc gagtgttccc gaaccttaaa cgcacagatt atgattaatg caagaattgg     480
catacatcac ctcaaatctc ggcttcgcaa aaagagcgtt gcgagccaac gcacagcccg     540
actcggcgca cgcacccctcg ctcccgcttc cttgctagtg catttgaaag cccacagaca     600
ctattttcag gccgaatacg cgctgcgagg agcttccagg cgactttctc gccgcatgag     660
cacacgtgcg ctgtacggca ccatggggg cctcgcttct gtttccactg ttcacgcgcg     720
ttcagttgtg gccgacaata accaattctt gatagtaacc agcctggtcg cgttcaagcg     780
caggtgagca catgttgctg cggagcgcga gcgccgctgt tgaatcgcga gcaagggttt     840
gtggtcacgg cggcttggcc gctgcatgcg cgccgagcgt ctgctcagtt gatagatgtc     900
atgctcatga gcatcgcgac agtcagcacc ggtggagagc ctcttcggcg accacaaaaa     960
ctgatggaag ttctcgcgcg tcttggtcgc aggcaccaaa atg                       1003
```

<210> SEQ ID NO 22
<211> LENGTH: 1124
<212> TYPE: DNA
<213> ORGANISM: Chlamydamonas reinhardtii

<400> SEQUENCE: 22

| | | | | | |
|---|---|---|---|---|---|
| gcgtcctccg | ctgtcacatc | gtaactgcgc | cgttgcgctt | gcgactttgg | tcgagaacgg | 60 |
| acgttgcggc | ggctgagtgg | aggctcgcac | agctgccggt | gtgttttgtg | gcctaggtat | 120 |
| gcccgaggcc | ccggtgtgct | tgcgcccccc | cccaagaaaa | ggaggagtcg | acgatgtac | 180 |
| tgagtgcaca | ccttgccact | gccagggcgt | ggaaatgctg | tagggcggt | gcgaagcgat | 240 |
| gcctggtatc | acactaggga | ttctaggggg | gacatgtgca | tgtgtgtgcg | cgcaattgct | 300 |
| gggcggggac | tgtgttattg | tgtgttcggg | aggttaaaag | gagtgcttaa | gtagttgtcg | 360 |
| gcacctatag | ctgcagtacc | agtagcctgc | tgggctcccc | atcccacata | catgtgagct | 420 |
| tttaagcaca | cgcagagggt | tcgcatcgca | tcagtctcgc | actgttcgga | acgggccatg | 480 |
| cttaaccttc | ttgaagcacg | tgcgccgttt | cgtgcatgtt | ctgggctgag | tgagcggctt | 540 |
| tcacgcatga | tcattaccaa | cagcaattgg | actttctgct | catggagccg | gcagatcgga | 600 |
| cgcaatactt | gaccacacac | acgccggcaa | cttgtgccct | atatggcctg | gcgagttga | 660 |
| acgcgcaagg | aggagttggg | cgcgagagag | gatctgaggc | cgacatgaca | acgcacattg | 720 |
| ttttactaat | gggactgtac | gtaaagaact | tttgagttg | atggtatatc | cggggatttt | 780 |
| ggagtgcagg | agagggtgct | cagatggaaa | gcacacgcgg | ggcctctcaa | cgtgtcatga | 840 |
| acgacacatt | attgcaagga | attgtgtcag | ggggcatctt | ggagaaaggg | cgtggcggga | 900 |
| gatgccgggc | ttctagacca | gggatgtata | taactctgtg | cggttgttgc | aacggtgctt | 960 |
| gaggcttgga | ccgtaatgtt | gcggctgaaa | aggaggagtc | cacacagggc | gtcagacggc | 1020 |
| cggaaaactt | gtttcactca | cgcgcggcgc | ataccctgcag | cgcatgcgaa | gcgcacagtc | 1080 |
| tgccgtccaa | agattttgat | cagcattgta | agcactgtct | atga | | 1124 |

<210> SEQ ID NO 23
<211> LENGTH: 1022
<212> TYPE: DNA
<213> ORGANISM: Chlamydamonas reinhardtii

<400> SEQUENCE: 23

| | | | | | |
|---|---|---|---|---|---|
| agcagttaca | ttctgctctg | tgccggcggc | acaatggcga | acgacccggg | gatgtttgcg | 60 |
| cgctcgctgc | gcccggtgtg | tgagagctga | ggcggaccgg | cgagccaggg | acgcagtgcc | 120 |
| aacgcaccgc | tgtggaactt | ctctgcgcgc | gacccgggtg | cgccacgagg | gggtgccaca | 180 |
| attgtaagac | acaacgtcac | aaccgcccag | gcccctcgca | catgcctcga | cccgcaccct | 240 |
| catggacgat | gtcctggcct | gagaacagga | gcgaatacac | gactttagcc | aatgcttcag | 300 |
| gtgtgcctgc | gggcctggcc | gtcgcggctc | gaggtgtgga | aggaagggct | tcgaccatgc | 360 |
| gcgtcgccac | gacagagctc | ctcctctatt | tgctggacct | cccctacaga | caccatacgc | 420 |
| gtgtaacttg | ctggggcgcc | gagaagcaag | cgtaagccct | cgcgtcagtc | ggggaaggag | 480 |
| cacaaggtgt | ggcacatgga | tagcgtgtcg | acctcggctg | ggtgcgtcga | aatcgtcatg | 540 |
| agtggtatct | gcttaaatgc | ctcgactacc | gctttccaca | gactcaagcg | ctgtcgtttt | 600 |
| ctctgaagtt | ctcccactga | cggtctcgtt | agcgtaactc | cctcggcgt | tgccgaaatg | 660 |
| ccctcatgct | ttgcatggtt | caatactatg | tttatttaca | tgactactgg | catcggaaca | 720 |
| actttggaag | gaggccccag | ggcaaatcga | gaagtttggt | tacgcagaag | ctcgctagca | 780 |

| | |
|---|---|
| agtcccgcct ctgcgggcgc cattcacaca acttactatg aacgcctctg ctctccataa | 840 |
| tgcgtttgag aacctctcga cacggggggcc tccccccaca cccctgtcac accagcccca | 900 |
| caccgggcgc cgtactaacg cacatgacgg aatgggcctc ctccttttcc tcgtgggctt | 960 |
| aaattcagtc gggcgagaga tttggtaacc ttgatttcgc ggaactcagg ccggcaacca | 1020 |
| tg | 1022 |

<210> SEQ ID NO 24
<211> LENGTH: 1427
<212> TYPE: DNA
<213> ORGANISM: Chlamydamonas reinhardtii

<400> SEQUENCE: 24

| | |
|---|---|
| agcggcagac tcgttcggtg ctcggcggac aagacacgtt agtaaaagag atgaagtaag | 60 |
| acgctgcggt tgcagtcggc gggggcagcg gctccgcggc cgactgcgtg aactgatgaa | 120 |
| tgaatgagtg aggcggagcc ggaagccagg aacgcttggg agtcctggca atggtttgtg | 180 |
| ccttgaggct cggcttggct tgcgtgagcg agcgtgcaga gtgaggcgcg ccatgagcgc | 240 |
| gtcgcctttg tcttgcggta ttgtgaattg acctgcttgt ggcttgggcc gcgttgggga | 300 |
| tgtccggaag tgcgtccacg gctatgatcg gggtgggtta cccatggtcg tgggtgtctc | 360 |
| tatgagcgct gaagcgcaac tgctgctggg cggagttgaa actgctgaga agtccgtggg | 420 |
| gagagcgtgt tcacacacga acacacaaat acacacatgg tgtgcgtgtg cactgattct | 480 |
| tgcccgtatg ggccctggga ttgtagcgcc agtgggagtt gttagggcgt ccctgagaga | 540 |
| tttgtgcacg gcgcatatga ggcggcagca ggaattcccc gccgcgccgt acgcgtgggt | 600 |
| ggtcggacag atggtggcag tcgcaggcag taactagcgt ttttgtttgt gtttgtgcgc | 660 |
| acgccctgtg tactgagttg gccaccgcag ggtggccact gtacggtatt ttacgagtgc | 720 |
| cagggctgca ccagtcaggc tttcagttac acatggacta gatagcatta cacacggacg | 780 |
| gtacctgagt accaagaatc aagctattag caatattacg aatgtcggga accggattgg | 840 |
| gcgcacgtac acatcattag aagtccgcat gtgtgacgtg tgtatggcat cgggatgcaa | 900 |
| ggaaatccat gtgcttgccg gactgtcggt ttgagtgcat catagcggat tcccatgcaa | 960 |
| taaggcattt gcggcggctt gctagaccac atactgctgc tgctgcacgg tcaaggcacg | 1020 |
| gcagcggcat gcaggggtta gcatgcgaag gcatttgtg ttactcaggc tgtccgcgca | 1080 |
| tgggtttgtc ttggtgtggt gacggcattg tggtaatatc gggatggcat tagctgcaag | 1140 |
| cagcaaaagc atgatgctag atagcaagca cggatgtggc ggacagtgtt gaagcaaaca | 1200 |
| cgtttggcag ggttgtggat gagttgactg cgcaggtcgt tgcaaaccgt tgaggcaaca | 1260 |
| gttcggtttg cggcagtcgg tagcatcaag ttcatggcta aataggcgag ccggcgatta | 1320 |
| catcgcatct acttacgtgc gtgacctacg tggtacatgg cccataccac aattacacat | 1380 |
| cgaacaggca catcctcaac atactgtaac atactaacat tccccag | 1427 |

<210> SEQ ID NO 25
<211> LENGTH: 1836
<212> TYPE: DNA
<213> ORGANISM: Olea europaea

<400> SEQUENCE: 25

| | |
|---|---|
| atgacgatcc cggagttgcc ggagagttta gaaacgacga cgttgaattc ccaccacagc | 60 |
| cgcgccgcga gtactgttcg gcggagatct attgacgtgg cagtactgga gtcagattca | 120 |

```
aactctttag aggcggtgaa tgatagtgac agcgatgtta ataacactaa tgagatggga    180
aatctgcgtg gaggagtggt ggaatcggcg ctggaagagc cgagtgaatt gggtactgaa    240
ggtttgagaa atggcaagga ggagaacgag catgttcgta ccggagagag taatcaagaa    300
atggaggtgt tggcgtcggc gaaattcgcg caccggccgt cggcaccggt tcaccggaga    360
atcaaagaga gtcctctcag ctcggacgca atcttcaaac agagtcatgc gggcctcttc    420
aacctctgta tagtggtgct tgttgctgta aatagcagac ttattattga aaatttgatg    480
aagtatggct ggctgatcaa ttcaggcttt tggtttagtt caacatcact gaaggattgg    540
ccacttctaa tgtgctgcct gagtctccca attttccgc ttgctgcatt ttttgttgag    600
aagttggtac tactcaagta tatatctgaa tgtgttgctg tctttcttca cattttaata    660
acaacagctg ctatcttgta tccggttttg gttattctta ggtgtgattc tgctgttctg    720
tctggcgtca cattaatgct ctttgcttgc attgtgtggt tgaagttggt atcttatgct    780
catgcaagtc acgatatgag ggcactagcc aaatcacttg ataagggtga acattgtct    840
ggttattgga actcggatga ctcttacggt gctagcttcc agagtttggc atacttcatg    900
gttgctccca cattgtgtta ccagcctagc tatccccgta catcgtgcat tcggaagggt    960
tgggtggtac gtcaactcat taagttaata atatttacag gattcatggg atttatcgta   1020
gaacagtaca taaatccaat tgtgcgaaat tctcaacatc ctttgaaagg aaaccttttg   1080
tatgccatag aaagagtctt gaagctttca gttccaaatt tatatgtgtg gctctgcatg   1140
ttttattgtt ttttccatct ttggctgaat atattagcgg aacttctctg ctttggtgat   1200
cgtgagttct acaaagattg gtggaatgcg aaaacagttg aggagtattg gaggatgtgg   1260
aatatgcctg tacacaagtg gatggtccga catatatatt ttccatgctt aaggaatggg   1320
atgcctaggg gcggtgctat tctgatagcg ttccttatat ctgctatttt tcatgagttg   1380
tgtattgccg tcccttgcca catattcaag ttttgggcat tcattggcat tatgtttcag   1440
gttcctcttg ttatcttaac caactacttg caagacaagt ttcaaaattc aatggtgggc   1500
aacatgatat tttggtgctt tttcagcata ctaggtcaac ccatgtgttt actgttatat   1560
taccatgact tgatgaatcg aaaagctagt gcaaaataag gccctgccac aaatttgcta   1620
aacgatggtg attccattgg gggtacaaat tgcagcaact gggttgctat tccccacat    1680
gtttccatac tggttttcgc gcagcttcct catctgccct ggcgaagacg agacatgaag   1740
ggaacgaact aaacttaggg caatacagtt ttggttgaaa atgtaacata ttggcatttt   1800
gttggttact ttggatgtgg acattttat gatgag                              1836
```

<210> SEQ ID NO 26
<211> LENGTH: 532
<212> TYPE: PRT
<213> ORGANISM: Olea europaea

<400> SEQUENCE: 26

Met Thr Ile Pro Glu Leu Pro Glu Ser Leu Glu Thr Thr Thr Leu Asn
1               5                   10                  15

Ser His His Ser Arg Ala Ala Ser Thr Val Arg Arg Ser Ile Asp
            20                  25                  30

Val Ala Val Leu Glu Ser Asp Ser Asn Ser Leu Glu Val Asn Asp
        35                  40                  45

Ser Asp Ser Asp Val Asn Asn Thr Asn Glu Met Gly Asn Leu Arg Gly
    50                  55                  60

Gly Val Val Glu Ser Ala Leu Glu Glu Pro Ser Glu Leu Gly Thr Glu

-continued

```
             65                  70                  75                  80
Gly Leu Arg Asn Gly Lys Glu Glu Asn Glu His Val Arg Thr Gly Glu
                     85                  90                  95
Ser Asn Gln Glu Met Glu Val Leu Ala Ser Ala Lys Phe Ala His Arg
                    100                 105                 110
Pro Ser Ala Pro Val His Arg Ile Lys Glu Ser Pro Leu Ser Ser
            115                 120                 125
Asp Ala Ile Phe Lys Gln Ser His Ala Gly Leu Phe Asn Leu Cys Ile
            130                 135                 140
Val Val Leu Val Ala Val Asn Ser Arg Leu Ile Ile Glu Asn Leu Met
145                 150                 155                 160
Lys Tyr Gly Trp Leu Ile Asn Ser Gly Phe Trp Ser Ser Thr Ser
                165                 170                 175
Leu Lys Asp Trp Pro Leu Leu Met Cys Cys Leu Ser Leu Pro Ile Phe
            180                 185                 190
Pro Leu Ala Ala Phe Phe Val Glu Lys Leu Val Leu Lys Tyr Ile
        195                 200                 205
Ser Glu Cys Val Ala Val Phe Leu His Ile Leu Ile Thr Thr Ala Ala
        210                 215                 220
Ile Leu Tyr Pro Val Leu Val Ile Leu Arg Cys Asp Ser Ala Val Leu
225                 230                 235                 240
Ser Gly Val Thr Leu Met Leu Phe Ala Cys Ile Val Trp Leu Lys Leu
                245                 250                 255
Val Ser Tyr Ala His Ala Ser His Asp Met Arg Ala Leu Ala Lys Ser
            260                 265                 270
Leu Asp Lys Gly Glu Thr Leu Ser Gly Tyr Trp Asn Ser Asp Ser
        275                 280                 285
Tyr Gly Ala Ser Phe Gln Ser Leu Ala Tyr Phe Met Val Ala Pro Thr
        290                 295                 300
Leu Cys Tyr Gln Pro Ser Tyr Pro Arg Thr Ser Cys Ile Arg Lys Gly
305                 310                 315                 320
Trp Val Val Arg Gln Leu Ile Lys Leu Ile Ile Phe Thr Gly Phe Met
                325                 330                 335
Gly Phe Ile Val Glu Gln Tyr Ile Asn Pro Ile Val Arg Asn Ser Gln
            340                 345                 350
His Pro Leu Lys Gly Asn Leu Leu Tyr Ala Ile Glu Arg Val Leu Lys
        355                 360                 365
Leu Ser Val Pro Asn Leu Tyr Val Trp Leu Cys Met Phe Tyr Cys Phe
        370                 375                 380
Phe His Leu Trp Leu Asn Ile Leu Ala Glu Leu Leu Cys Phe Gly Asp
385                 390                 395                 400
Arg Glu Phe Tyr Lys Asp Trp Asn Ala Lys Thr Val Glu Glu Tyr
                405                 410                 415
Trp Arg Met Trp Asn Met Pro Val His Lys Trp Met Val Arg His Ile
                420                 425                 430
Tyr Phe Pro Cys Leu Arg Asn Gly Met Pro Arg Gly Gly Ala Ile Leu
            435                 440                 445
Ile Ala Phe Leu Ile Ser Ala Ile Phe His Glu Leu Cys Ile Ala Val
        450                 455                 460
Pro Cys His Ile Phe Lys Phe Trp Ala Phe Ile Gly Ile Met Phe Gln
465                 470                 475                 480
Val Pro Leu Val Ile Leu Thr Asn Tyr Leu Gln Asp Lys Phe Gln Asn
                485                 490                 495
```

```
Ser Met Val Gly Asn Met Ile Phe Trp Cys Phe Phe Ser Ile Leu Gly
            500                 505                 510

Gln Pro Met Cys Leu Leu Leu Tyr Tyr His Asp Leu Met Asn Arg Lys
        515                 520                 525

Ala Ser Ala Lys
    530
```